(12) United States Patent
Renner et al.

(10) Patent No.: US 8,999,342 B2
(45) Date of Patent: Apr. 7, 2015

(54) ANTI-FIBROBLAST ACTIVATION PROTEIN ANTIBODIES AND METHODS AND USES THEREOF

(75) Inventors: Christoph Renner, Zürich (CH); Eliane Fischer, Villigen PSI (CH); Stefan Bauer, Heidelberg (DE); Thomas Wüest, Zürich (CH)

(73) Assignee: Ludwig Institute for Cancer Research, Ltd., New York, NY (US)

( * ) Notice: Subject to any disclaimer, the term of this patent is extended or adjusted under 35 U.S.C. 154(b) by 0 days.

(21) Appl. No.: 13/499,718

(22) PCT Filed: Oct. 1, 2010

(86) PCT No.: PCT/US2010/002660
§ 371 (c)(1),
(2), (4) Date: Jun. 22, 2012

(87) PCT Pub. No.: WO2011/040972
PCT Pub. Date: Apr. 7, 2011

(65) Prior Publication Data
US 2012/0258119 A1  Oct. 11, 2012

Related U.S. Application Data

(60) Provisional application No. 61/278,064, filed on Oct. 2, 2009.

(51) Int. Cl.
| | | |
|---|---|---|
| A61K 39/395 | (2006.01) |
| C12P 21/08 | (2006.01) |
| C07K 16/00 | (2006.01) |
| C07K 16/40 | (2006.01) |

(52) U.S. Cl.
CPC ............. *C07K 16/40* (2013.01); *C07K 2317/21* (2013.01); *C07K 2317/55* (2013.01); *C07K 2317/92* (2013.01); *C07K 2317/73* (2013.01); *C07K 2317/33* (2013.01); *C07K 2317/76* (2013.01); *C07K 2317/77* (2013.01)

(58) Field of Classification Search
None
See application file for complete search history.

(56) References Cited

U.S. PATENT DOCUMENTS 5,587,299 A   12/1996   Rettig et al.

FOREIGN PATENT DOCUMENTS

WO    1806365    7/2001

OTHER PUBLICATIONS

Brocks et al. Species-cross reactive scFv against the tumor stroma marker "fibroblast activation protein" selected by phage display from an immunized FAP-/- knock-out mouse. Molecular Medicine. 7(7): 461-469, 2001.*
Paul. Fundamental Immunology, 3rd Edition, Raven Press, New York, Chapter 8, pp. 292-295, 1993.*
MacCallum et al. Antibody-antigen interactions: contact analysis and binding site topography. Journal of Molecular Biology. 1996; 262:732-745.*
Casset et al. A peptide mimetic of an anti-CD4 monoclonal antibody by rational design. Biochemical and Biophysical Research Communications. 2003; 307:198-205, 2003.*
Brown et al. Tolerance to single, but not multiple, amino acid replacements in antibody VH CDR2. Journal of Immunology. May 1996;156(9):3285-91.*
Rudikoff et al. Single amino acid substitution altering antigen-binding specificty. PNAS. 1982; 79(6):1979-1983.*
Colman. Effects of amino acid sequence changes on antibody-antigen interactions. Research in Immunology. 1994; 145:33-36.*
Brocks et al. Species-cross reactive scFv against the tumor stroma marker "fibroblast activation protein" selected by phage display from an immunized FAP-/- knock-out mouse. Molecular Medicine. 2001; 7(7): 461-469.*
Acharya, PS et al (2006) Fibroblast activation protein: a serine protease expressed at the remodeling interface in idiopathic pulmonary fibrosis Hum Pathol 37(3):352-360.
Aertgeerts, K et al (2005) Structural and kinetic analysis of the substrate specificity of human fibroblast activation protein alpha J Biol Chem 280(20):19441-19444.
Arscott, WT et al (2009) Suppression of neuroblastoma growth by dipeptidyl peptidase IV: relevance of chemokine regulation and caspase activation Oncogene 28(4):479-491.
Artym, VV et al (2002) Molecular proximity of seprase and the urokinase-type plasminogen activator receptor on malignant melanoma cell membranes: dependence on beta1 integrins and the cytoskeleton Carcinogenesis 23 (10):1593-1601.
Bauer, S et al (2006) Fibroblast activation protein is expressed by rheumatoid myofibroblast-like synoviocytes Arthritis Res Ther. 8(6):R171.
Brocks, B et al (2001) Species-crossreactive scFv against the tumor stroma marker "fibroblast activation protein" selected by phage display from an immunized FAP-/- knock-out mouse Mol Med 7(7):461-469.
Chen, WT et al (2003) DPPIV, seprase, and related serine peptidases in multiple cellular functions Curr Top Dev Biol 54:207-232.
Chen, H et al (2009) TGF-beta-induced fibroblast activation protein expression, fibroblast activation protein expression increases the proliferation, adhesion, and migration of HO-8910PM Exp and Molec Pathology, doi:10.1016/j.yexmp.2009.09.001.

(Continued)

*Primary Examiner* — Vanessa L. Ford
*Assistant Examiner* — Sandra Dillahunt
(74) *Attorney, Agent, or Firm* — Klauber & Jackson, LLC

(57) ABSTRACT

Specific binding members, particularly antibodies and fragments thereof, which bind to Fibroblast Activation Protein (FAP) are provided, particularly recognizing both human and mouse FAP. These antibodies are useful in the diagnosis and treatment of conditions associated with activated stroma, including wound healing, epithelial cancers, osteoarthritis, rheumatoid arthritis, cirrhosis and pulmonary fibrosis. The anti-FAP antibodies, variable regions or CDR domain sequences thereof, and fragments thereof may also be used in therapy in combination with chemotherapeutics, immune modulators, or anti-cancer agents and/or with other antibodies or fragments thereof. Antibodies of this type are exemplified by the novel antibodies ESC1 1 and ESC 14 whose sequences are provided herein.

9 Claims, 12 Drawing Sheets

(56) References Cited

OTHER PUBLICATIONS

Cheng, JD et al (2002) Promotion of tumor growth by murine fibroblast activation protein, a serine protease, in an animal model Cancer Res 62(16):4767-4772.
Cheng, JD et al (2003) Tumors and their microenvironments: tilling the soil Clin Cancer Res. 9(5):1590-1595.
Cheng, JD et al (2005) Abrogation of fibroblast activation protein enzymatic activity attenuates tumor growth Mol Cancer Ther 4(3):351-360.
Cohen, SJ et al (2008) Fibroblast activation protein and its relationship to clinical outcome in pancreatic adenocarcinoma Pancreas 37(2):154-158.
Edosada, CY et al (2006) Selective inhibition of fibroblast activation protein protease based on dipeptide substrate specificity J Biol Chem 281(11):7437-7444.
Friedl, P et al (2009) Proteolytic interstitial cell migration: a five-step process Cancer Metastasis Rev 28(1-2):129-135.
Garin-Chesa, P et al (1990) Cell surface glycoprotein of reactive stromal fibroblasts as a potential antibody target in human epithelial cancers Proc Natl Acad Sci USA 87(18):7235-7239.
Ghersi, G et al (2002) Regulation of fibroblast migration on collagenous matrix by a cell surface peptidase complex J Biol Chem 277(32):29231-29241.
Ghersi, G et al (2006) The protease complex consisting of dipeptidyl peptidase IV and seprase plays a role in the migration and invasion of human endothelial cells in collagenous matrices. Cancer Res 66(9):4652-4661.
Goldstein, LA et al (1997) Molecular cloning of seprase: a serine integral membrane protease from human melanoma Biochim Biophys Acta 1361(1):11-19.
Henry, LR et al (2007) Clinical implications of fibroblast activation protein in patients with colon cancer Clin Cancer Res 13(6):1736-1741.
Hofheinz, RD et al (2003) Stromal antigen targeting by a humanised monoclonal antibody: an early phase II trial of sibrotuzumab in patients with metastatic colorectal cancer Onkologie 26(1):44-48.
Inamoto, T et al (2007) Humanized anti-CD26 monoclonal antibody as a treatment for malignant mesothelioma tumors. Clin Cancer Res 13(14):4191-4200.
Kelly, T (1999) Evaluation of seprase activity Clin Exp Metastasis 17(1):57-62.
Kennedy, A et al (2009) Elevation of seprase expression and promotion of an invasive phenotype by collagenous matrices in ovarian tumor cells. Int J Cancer 124(1):27-35.
Lee, KN et al (2006) Antiplasmin-cleaving enzyme is a soluble form of fibroblast activation protein. Blood, 107 (4):1397-1404.
Levy, CE et al (1999) Conductive hearing loss in individuals with fibrodysplasia ossificans progressive Am J Audiol 8 (1):29-33.
Loster, K et al (1995) The cysteine-rich region of dipeptidyl peptidase IV (CD 26) is the collagen-binding site Biochem Biophys Res Commun 217(1):341-348.
Monsky, WL et al (1994) A potential marker protease of invasiveness, seprase, is localized on invadopodia of human malignant melanoma cells Cancer Res 54(21):5702-5710.
Morimoto, C et al (1994) Role of CD26/dipeptidyl peptidase IV in human immunodeficiency virus type 1 infection and apoptosis Proc Natl Acad Sci USA 91(21):9960-9964.
Niedermeyer, J et al (1998) Mouse fibroblast-activation protein—conserved Fap gene organization and biochemical function as a serine protease Eur J Biochem 254(3):650-654.
O'Brien, P et al (2008) Seprase: an overview of an important matrix serine protease Biochim Biophys Acta 1784 (9):1130-1145.
Ostermann, E et al (2008) Effective immunoconjugate therapy in cancer models targeting a serine protease of tumor fibroblasts Clin Cancer Res.14(14):4584-4592.
Park, JE et al (1999) Fibroblast activation protein, a dual specificity serine protease expressed in reactive human tumor stromal fibroblasts J Biol Chem 274(51):36505-36512.
Pineiro-Sanchez, ML et al (1997) Identification of the 170-kDa melanoma membrane bound gelatinase (seprase) as a serine integral membrane protease J Biol Chem 272(12):7595-7601.
Ramirez-Montagut, T et al (2004) FAPalpha, a surface peptidase expressed during wound healing, is a tumor suppressor Oncogene 2004. 23(32):5435-5446.
Rettig, WJ et al (1988) Cell-surface glycoproteins of human sarcomas: differential expression in normal and malignant tissues and cultured cells Proc Natl Acad Sci USA 85(9):3110-3114.
Rettig, WJ et al (1993) Regulation and heteromeric structure of the fibroblast activation protein in normal and transformed cells of mesenchymal and neuroectodermal origin Cancer Res 53(14):3327-3335.
Rettig, WJ et al (1994) Fibroblast activation protein: purification, epitope mapping and induction by growth factors Int J Cancer. 58(3):385-392.
Scanlan, MJ et al (1994) Molecular cloning of fibroblast activation protein alpha, a member of the serine protease family selectively expressed in stromal fibroblast of epithelial cancers Proc Natl Acad Sci USA 91(12):5657-5661.
Scott, AM et al (2003) A Phase I dose-escalation study of sibrotuzumab in patients with advanced or metastatic fibroblast activation protein-positive cancer. Clin Cancer Res 9(5):1639-1647.
Wang, XM et al (2005) Fibroblast activation protein increases apoptosis, celladhesion, and migration by the LX-2 human stellate cell line Hepatology 42(4):935-945.
Welt, S et al (1994) Antibody targeting in metastatic colon cancer: a phase I study of monoclonal antibody F19 against a cell-surface protein of reactive tumor stromal fibroblasts J Clin Oncol 12(6):1193-1203.
Wesley, UV et al (1999) A role for dipeptidyl peptidase IV in suppressing the malignant phenotype of melanocytic cells J Exp Med 190(3):311-322.
Wolf, BB et al (2008) On the edge of validation—cancer protease fibroblast activation protein Mini Rev Med Chem 8(7):719-727.

\* cited by examiner

FIGURE 2A

A. ESC11 ANTIBODY

HEAVY CHAIN SEQUENCE

DNA sequence
CACGTGCAGCTGCAGGAGTCGGGCCCAGGACTGGTGAAGCCTTCGGAGACCCTGTCCCTCACCTGCACTGTCTCTGGTGGCTC
CATCAGCAGTAATAATTACTACTGGGGCTGGATCCGCCAGACCCCAGGGAAGGGGCTGGAGTGGATTGGGAGTATCTATTAC
AGTGGGAGCACCAACTACAACCCGTCCCTCAAGAGTCGAGTCACCATATCAGTAGACACGTCCAAGAACCAGTTCTCCCTGAA
GCTGAGCTCTGTGACCGCCGCGGACACGGCTGTGTATTACTGTGCGAGAGGCGCCCGGTGGCAAGCCCGACCCGCAACCAGG
ATAGATGGAGTCGCTTTTGATATCTGGGGCCAAGGGACAATGGTCACCGTCTCAAGC

Peptide sequence
HVQLQESGPGLVKPSETLSLTCTVSGGSISSNNYYWGWIRQTPGKGLEWIGSIYYSGSTNYNPSLKSRVTISVDTSKNQFSLKLSSVTA
ADTAVYYCARGARWQARPATRIDGVAFDIWGQGTMVTVSS

Modified for eukaryotic expression:
DNA sequence
CAGGTGCAGCTGCAGGAGTCGGGCCCAGGACTGGTGAAGCCTTCGGAGACCCTGTCCCTCACCTGCACTGTCTCTGGTGGCTC
CATCAGCAGTAATAATTACTACTGGGGCTGGATCCGCCAGACCCCAGGGAAGGGGCTGGAGTGGATTGGGAGTATCTATTAC
AGTGGGAGCACCAACTACAACCCGTCCCTCAAGAGTCGAGTCACCATATCAGTAGACACGTCCAAGAACCAGTTCTCCCTGAA
GCTGAGCTCTGTGACCGCCGCGGACACGGCTGTGTATTACTGTGCGAGAGGCGCCCGGTGGCAAGCCCGACCCGCAACCAGG
ATAGATGGAGTCGCTTTTGATATCTGGGGCCAAGGGACAATGGTCACCGTCTCAAGC

Peptide sequence
EVQLQESGPGLVKPSETLSLTCTVSGGSISSNNYYWGWIRQTPGKGLEWIGSIYYSGSTNYNPSLKSRVTISVDTSKNQFSLKLSSVTA
ADTAVYYCARGARWQARPATRIDGVAFDIWGQGTMVTVSS

LIGHT CHAIN SEQUENCE

DNA sequence
GAAACGACACTCACGCAGTCTCCAGGCACCCTGTCTTTGTCTCCAGGGGAAAGAGCCACCCTCTCCTGCAGGGCCAGTCAGAC
TGTTACCCGCAACTACTTAGCCTGGTACCAGCAGAAACCTGGCCAGGCTCCCAGGCTCCTCATGTATGGTGCATCCAACAGGG
CCGCTGGCGTCCCAGACAGGTTCAGTGGCAGTGGGTCTGGGACAGACTTCACTCTCACCATCAGCAGACTGGAGCCTGAAGAT
TTTGCAGTGTATTACTGTCAGCAGTTTGGTAGCCCGTACACTTTTGGCCAGGGGACCAAGGTGGAGATCAAA

Peptide sequence
ETTLTQSPGTLSLSPGERATLSCRASQTVTRNYLAWYQQKPGQAPRLLMYGASNRAAGVPDRFSGSGSGTDFTLTISRLEPEDFAVY
YCQQFGSPYTFGQGTKVEIK

FIGURE 2B

B. ESC14 ANTIBODY

HEAVY CHAIN SEQUENCE

DNA sequence

GAGGTCCAGCTGGTGCAGTCTGGAGCTGAGGTGAAGAAGCCTGGGGCCTCAGTGAAGGTCTCCTGCAAGGNTTCTGGTTACA
CCTTTACCAGCTATGGTATCAGCTGGGTGCGACAGGCCCCTGGACAAGGGCTTGAGTGGATGGGATGGATCAGCGCTTACAA
TGGTAACACAAACTATGCACAGAAGCTCCAGGGCAGAGTCACCATGACCACAGACACATCCACGAGCACAGCCTACATGGAG
CTGAGGAGCCTGAGATCTGACGACACGGCCGTGTATTACTGTGCGAGAGATTGGAGTCGTAGTGGTTATTACTTACCTGACTA
CTGGGGCCAGGGCACCCTGGTCACCGTCTCAAGC

Peptide sequence

EVQLVQSGAEVKKPGASVKVSCKASGYTFTSYGISWVRQAPGQGLEWMGWISAYNGNTNYAQKLQGRVTMTTDTSTSTAYMEL
RSLRSDDTAVYYCARDWSRSGYYLPDYWGQGTLVTVSS

LIGHT CHAIN SEQUENCE

DNA sequence

GATGTTGTGATGACTCAGTCTCCACTCTCCCTGCCCGTCACCCTTGGACAGCCGGCCTCCATCTCCTGCAGGTCTAGTCAGAGTC
TCCTGCATAGCAATGGATACAACTATTTGGATTGGTACCTGCAGAGGCCAGGGCAGTCTCCACACCTCCTGATCTTTTTGGGTT
CTAATCGGGCCTCCGGGGTCCCTGACAGGTTCAGTGGCAGTGGCTCAGGCACAGATTTTACACTGAAAATCAGCAGAGTGGA
GGCTGAGGATGTTGGGATTTATTACTGCATGCAAGCTCTACAAACTCCTCCGACGTTCGGCCAAGGGACCAAGGTGGAAATCA
AA

Peptide sequence

DVVMTQSPLSLPVTLGQPASISCRSSQSLLHSNGYNYLDWYLQRPGQSPHLLIFLGSNRASGVPDRFSGSGSGTDFTLKISRVEAEDV
GIYYCMQALQTPPTFGQGTKVEIK

FIGURE 10

FAP antibody alignment

A

Heavy chain

```
                                         CDR I                      CDR II

ESC11   1   QVQLQESGPGLVKPSETLSLTCTVSGGSISSNYYYWGWIRQTPGKGLEWIGSI-YYSGST   59
            +VQL +SG  + KP   ++ ++C  SG + +S  Y     W+RQ PG+GLEW+G I  Y+G+T
ESC14   1   EVQLVQSGAEVKKPGASVKVSCKASGYTFTS--YGISWVRQAPGQGLEWMGWISAYNGNT   58

CDR III
ESC11  60   NYNPSLKSRVTISVDTSKNQFSLKLSSVTAADTAVYYCARGARWQARPATRIDGVAFDIW  119
            NY    L+ RVT++ DTS +    ++L S+ + DTAVYYCAR   W      +R    D W
ESC14  59   NYAQKLQGRVTMTTDTSTSTAYMELRSLRSDDTAVYYCARD--W-----SRSGYYLPDYW  111

ESC11 120   GQGTMVTVSS   129
            GQGT+VTVSS
ESC14 112   GQGTLVTVSS   121
```

B

Light chain

```
                                         CDR I                      CDR II

ESC11   1   ETTLTQSPGTLSLSPGERATLSCRASQTVTR----NYLAWYQQKPGQAPRLLMYGASNRA   56
            +   +TQSP +L ++ G+ A++SCR+SQ++       NYL WY Q+PGQ+P LL++   SNRA
ESC14   1   DVVMTQSPLSLPVTLGQPASISCRSSQSLLHSNGYNYLDWYLQRPGQSPHLLIFLGSNRA   60

CDR III
ESC11  57   AGVPDRFSGSGSGTDFTLTISRLEPEDFAVYYCQQ-FGSPYTFGQGTKVEIK   107
            +GVPDRFSGSGSGTDFTL ISR+E ED +YYC Q  +P TFGQGTKVEIK
ESC14  61   SGVPDRFSGSGSGTDFTLKISRVEAEDVGIYYCMQALQTPPTFGQGTKVEIK   112
```

FIGURE 11
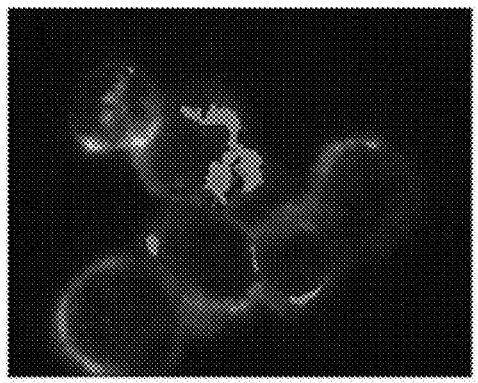
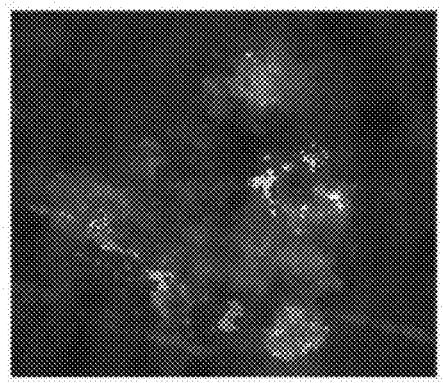
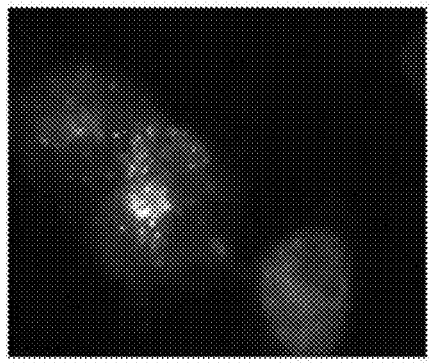

SEQUENCE LISTING

<160> NUMBER OF SEQ ID NOS: 22

<210> SEQ ID NO 1
<211> LENGTH: 129
<212> TYPE: PRT
<213> ORGANISM: Homo sapiens

<400> SEQUENCE: 1

His Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Asn
            20                  25                  30

Asn Tyr Tyr Trp Gly Trp Ile Arg Gln Thr Pro Gly Lys Gly Leu Glu
        35                  40                  45

Trp Ile Gly Ser Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ala Arg Trp Gln Ala Arg Pro Ala Thr Arg Ile Asp
            100                 105                 110

Gly Val Ala Phe Asp Ile Trp Gly Gln Gly Thr Met Val Thr Val Ser
        115                 120                 125

Ser

<210> SEQ ID NO 2
<211> LENGTH: 129
<212> TYPE: PRT
<213> ORGANISM: Homo sapiens

<400> SEQUENCE: 2

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Asn
            20                  25                  30

Asn Tyr Tyr Trp Gly Trp Ile Arg Gln Thr Pro Gly Lys Gly Leu Glu
        35                  40                  45

Trp Ile Gly Ser Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ala Arg Trp Gln Ala Arg Pro Ala Thr Arg Ile Asp
            100                 105                 110

Gly Val Ala Phe Asp Ile Trp Gly Gln Gly Thr Met Val Thr Val Ser
        115                 120                 125

Ser

<210> SEQ ID NO 3
<211> LENGTH: 107
<212> TYPE: PRT
<213> ORGANISM: Homo sapiens

<400> SEQUENCE: 3

Glu Thr Thr Leu Thr Gln Ser Pro Gly Thr Leu Ser Leu Ser Pro Gly

```
          1               5                  10                 15
        Glu Arg Ala Thr Leu Ser Cys Arg Ala Ser Gln Thr Val Thr Arg Asn
                        20                  25                 30
        Tyr Leu Ala Trp Tyr Gln Gln Lys Pro Gly Gln Ala Pro Arg Leu Leu
                        35                  40                 45
        Met Tyr Gly Ala Ser Asn Arg Ala Ala Gly Val Pro Asp Arg Phe Ser
                    50                  55                 60
        Gly Ser Gly Ser Gly Thr Asp Phe Thr Leu Thr Ile Ser Arg Leu Glu
         65                  70                  75                 80
        Pro Glu Asp Phe Ala Val Tyr Tyr Cys Gln Gln Phe Gly Ser Pro Tyr
                            85                  90                 95
        Thr Phe Gly Gln Gly Thr Lys Val Glu Ile Lys
                        100                 105
```

<210> SEQ ID NO 4
<211> LENGTH: 387
<212> TYPE: DNA
<213> ORGANISM: Homo sapiens

<400> SEQUENCE: 4

| | | |
|---|---|---|
| cacgtgcagc tgcaggagtc gggcccagga ctggtgaagc cttcggagac cctgtccctc | 60 |
| acctgcactg tctctggtgg ctccatcagc agtaataatt actactgggg ctggatccgc | 120 |
| cagaccccag ggaaggggct ggagtggatt gggagtatct attacagtgg gagcaccaac | 180 |
| tacaacccgt ccctcaagag tcgagtcacc atatcagtag acacgtccaa gaaccagttc | 240 |
| tccctgaagc tgagctctgt gaccgccgcg gacacggctg tgtattactg tgcgagaggc | 300 |
| gcccggtggc aagcccgacc cgcaaccagg atagatggag tcgcttttga tatctggggc | 360 |
| caagggacaa tggtcaccgt ctcaagc | 387 |

<210> SEQ ID NO 5
<211> LENGTH: 387
<212> TYPE: DNA
<213> ORGANISM: Homo sapiens

<400> SEQUENCE: 5

| | | |
|---|---|---|
| caggtgcagc tgcaggagtc gggcccagga ctggtgaagc cttcggagac cctgtccctc | 60 |
| acctgcactg tctctggtgg ctccatcagc agtaataatt actactgggg ctggatccgc | 120 |
| cagaccccag ggaaggggct ggagtggatt gggagtatct attacagtgg gagcaccaac | 180 |
| tacaacccgt ccctcaagag tcgagtcacc atatcagtag acacgtccaa gaaccagttc | 240 |
| tccctgaagc tgagctctgt gaccgccgcg gacacggctg tgtattactg tgcgagaggc | 300 |
| gcccggtggc aagcccgacc cgcaaccagg atagatggag tcgcttttga tatctggggc | 360 |
| caagggacaa tggtcaccgt ctcaagc | 387 |

<210> SEQ ID NO 6
<211> LENGTH: 321
<212> TYPE: DNA
<213> ORGANISM: Homo sapiens

<400> SEQUENCE: 6

| | | |
|---|---|---|
| gaaacgacac tcacgcagtc tccaggcacc ctgtctttgt ctccagggga aagagccacc | 60 |
| ctctcctgca gggccagtca gactgttacc gcaactact agcctggta ccagcagaaa | 120 |
| cctggccagg ctcccaggct cctcatgtat ggtgcatcca acagggccgc tggcgtccca | 180 |
| gacaggttca gtggcagtgg gtctgggaca gacttcactc tcaccatcag cagactggag | 240 |

```
cctgaagatt tgcagtgta ttactgtcag cagtttggta gcccgtacac ttttggccag      300
gggaccaagg tggagatcaa a                                                321

<210> SEQ ID NO 7
<211> LENGTH: 121
<212> TYPE: PRT
<213> ORGANISM: Homo sapiens

<400> SEQUENCE: 7

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Trp Ser Arg Ser Gly Tyr Tyr Leu Pro Asp Tyr Trp Gly
            100                 105                 110

Gln Gly Thr Leu Val Thr Val Ser Ser
        115                 120

<210> SEQ ID NO 8
<211> LENGTH: 112
<212> TYPE: PRT
<213> ORGANISM: Homo sapiens

<400> SEQUENCE: 8

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Arg Pro Gly Gln Ser
        35                  40                  45

Pro His Leu Leu Ile Phe Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Pro Thr Phe Gly Gln Gly Thr Lys Val Glu Ile Lys
            100                 105                 110

<210> SEQ ID NO 9
<211> LENGTH: 363
<212> TYPE: DNA
<213> ORGANISM: Homo sapiens
<220> FEATURE:
<221> NAME/KEY: variation
<222> LOCATION: 71
<223> OTHER INFORMATION: N can be A, C, T or G

<400> SEQUENCE: 9
gaggtccagc tggtgcagtc tggagctgag gtgaagaagc ctggggcctc agtgaaggtc      60
```

```
tcctgcaagg nttctggtta cacctttacc agctatggta tcagctgggt gcgacaggcc    120
cctggacaag ggcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gagagattgg    300
agtcgtagtg ttattactt acctgactac tggggccagg gcaccctggt caccgtctca    360
agc                                                                  363
```

<210> SEQ ID NO 10
<211> LENGTH: 336
<212> TYPE: DNA
<213> ORGANISM: Homo sapiens

<400> SEQUENCE: 10

```
gatgttgtga tgactcagtc tccactctcc ctgcccgtca cccttggaca gccggcctcc     60
atctcctgca ggtctagtca gagtctcctg catagcaatg gatacaacta tttggattgg    120
tacctgcaga ggccagggca gtctccacac ctcctgatct ttttgggttc taatcgggcc    180
tccggggtcc ctgacaggtt cagtggcagt ggctcaggca cagattttac actgaaaatc    240
agcagagtgg aggctgagga tgttgggatt tattactgca tgcaagctct acaaactcct    300
ccgacgttcg gccaagggac caaggtggaa atcaaa                              336
```

<210> SEQ ID NO 11
<211> LENGTH: 12
<212> TYPE: PRT
<213> ORGANISM: Homo sapiens

<400> SEQUENCE: 11

Gly Gly Ser Ile Ser Ser Asn Asn Tyr Tyr Trp Gly
 1               5                  10

<210> SEQ ID NO 12
<211> LENGTH: 16
<212> TYPE: PRT
<213> ORGANISM: Homo sapiens

<400> SEQUENCE: 12

Ser Ile Tyr Tyr Ser Gly Ser Thr Asn Tyr Asn Pro Ser Leu Lys Ser
 1               5                  10                  15

<210> SEQ ID NO 13
<211> LENGTH: 19
<212> TYPE: PRT
<213> ORGANISM: Homo sapiens

<400> SEQUENCE: 13

Gly Ala Arg Trp Gln Ala Arg Pro Ala Thr Arg Ile Asp Gly Val Ala
 1               5                  10                  15

Phe Asp Ile

<210> SEQ ID NO 14
<211> LENGTH: 10
<212> TYPE: PRT
<213> ORGANISM: Homo sapiens

<400> SEQUENCE: 14

Gly Tyr Thr Phe Thr Ser Tyr Gly Ile Ser
 1               5                  10

```
<210> SEQ ID NO 15
<211> LENGTH: 17
<212> TYPE: PRT
<213> ORGANISM: Homo sapiens

<400> SEQUENCE: 15

Trp Ile Ser Ala Tyr Asn Gly Asn Thr Asn Tyr Ala Gln Lys Leu Gln
1               5                   10                  15

Gly

<210> SEQ ID NO 16
<211> LENGTH: 12
<212> TYPE: PRT
<213> ORGANISM: Homo sapiens

<400> SEQUENCE: 16

Asp Trp Ser Arg Ser Gly Tyr Tyr Leu Pro Asp Tyr
1               5                   10

<210> SEQ ID NO 17
<211> LENGTH: 12
<212> TYPE: PRT
<213> ORGANISM: Homo sapiens

<400> SEQUENCE: 17

Arg Ala Ser Gln Thr Val Thr Arg Asn Tyr Leu Ala
1               5                   10

<210> SEQ ID NO 18
<211> LENGTH: 7
<212> TYPE: PRT
<213> ORGANISM: Homo sapiens

<400> SEQUENCE: 18

Gly Ala Ser Asn Arg Ala Ala
1               5

<210> SEQ ID NO 19
<211> LENGTH: 8
<212> TYPE: PRT
<213> ORGANISM: Homo sapiens

<400> SEQUENCE: 19

Gln Gln Phe Gly Ser Pro Tyr Thr
1               5

<210> SEQ ID NO 20
<211> LENGTH: 16
<212> TYPE: PRT
<213> ORGANISM: Homo sapiens

<400> SEQUENCE: 20

Arg Ser Ser Gln Ser Leu Leu His Ser Asn Gly Tyr Asn Tyr Leu Asp
1               5                   10                  15

<210> SEQ ID NO 21
<211> LENGTH: 7
<212> TYPE: PRT
<213> ORGANISM: Homo sapiens

<400> SEQUENCE: 21

Leu Gly Ser Asn Arg Ala Ser
1               5
```

```
<210> SEQ ID NO 22
<211> LENGTH: 9
<212> TYPE: PRT
<213> ORGANISM: Homo apiens

<400> SEQUENCE: 22

Met Gln Ala Leu Gln Thr Pro Pro Thr
 1               5
```

ANTI-FIBROBLAST ACTIVATION PROTEIN ANTIBODIES AND METHODS AND USES THEREOF

This application is a 371 of PCT/US10/02660 filed Oct. 1, 2010, which claims benefit of provisional application 61/278,064 filed Oct. 2, 2009.

FIELD OF THE INVENTION

The present invention relates to specific binding members, particularly antibodies and fragments thereof, which bind to Fibroblast Activation Protein (FAP), particularly recognizing both human and mouse FAP. These antibodies are useful in the diagnosis and treatment of conditions associated with activated stroma, including wound healing, epithelial cancers, osteoarthritis, rheumatoid arthritis, cirrhosis and pulmonary fibrosis. In addition, the can be used for the diagnosis and treatment of FAP positive tumors such as pancreatic cancer, melanoma and sarcomas. The antibodies, variable regions or CDR domain sequences thereof, and fragments thereof of the present invention may also be used in therapy in combination with chemotherapeutics, immune modulators, or anti-cancer agents and/or with other antibodies or fragments thereof.

BACKGROUND OF THE INVENTION

Fibroblast activation protein (FAP) was originally identified as a serine protease on reactive stromal fibroblasts [1, 2]. Subsequent molecular cloning revealed that FAP is identical to seprase, a 170 kDa membrane associated gelatinase that is expressed by melanoma cell lines [3, 4]. Full length cDNA encoded a type II transmembrane protease of 760 amino acids (aa) highly homologous to dipeptidyl peptidase IV (DPPIV) with a 52% aa identity over the entire sequence and almost 70% identity in the catalytic domain [3, 5]. U.S. Pat. No. 5,587,299, incorporated herein by reference, describes nucleic acid molecules encoding FAP and applications thereof.

FAP and DPPIV have similar gene sizes and are chromosomally adjacent to each other at 2q24, suggesting a gene duplication event (Genebank accession number U09278). Both proteins are members of the prolyl peptidase family [1, 6]. This class of enzymes is inducible, active on the cell surface or in extracellular fluids, and uniquely capable of cleaving N-terminal dipeptides from polypeptides with proline or alanine in the penultimate position [7]. DPPIV, also termed CD26, is constitutively expressed by several cell types including fibroblasts, endothelial and epithelial cells, leukocyte subsets like NK-cells, T-lymphocytes and macrophages. A small proportion of DPPIV circulates as soluble protein in the blood. In contrast to DPPIV, FAP is typically not expressed in normal adult tissue [1] and its proteolytically active soluble form is termed a2-Antiplasmin Cleaving Enzyme (APCE) [8]. Marked FAP expression occurs in conditions associated with activated stroma, including wound healing, epithelial cancers, osteoarthritis, rheumatoid arthritis, cirrhosis and pulmonary fibrosis [4, 9-11].

The FAP structure has been solved (PDB ID 1Z68) and is very similar to that of DPPIV [12]. FAP is anchored in the plasma membrane by an uncleaved signal sequence of approximately 20 amino acids and has a short, amino terminal, cytoplasmic domain of six amino acids [3-5]. The major part of the protein, including the catalytic domain, is exposed to the extracellular environment [13]. The FAP glycoprotein is a homodimer consisting of two identical 97-kDa subunits. Each FAP-monomer subunit consists of two domains, an $\alpha\beta$ hydrolase domain (aa 27-53 and 493-760) and an eight-blade $\beta$ propeller domain (aa 54-492) that enclose a large cavity. A small pocket within this cavity at the interface of both domains contains the catalytic triad (Ser624, Asp702 and His734) [12]. FAP gains its enzymatic activity upon homodimerization of the subunits [14] and beside its dipeptidyl peptidase activity, FAP also has collagen type I specific gelatinase [15] and endopeptidase activity [16]. The $\beta$ propeller acts as scaffolding for protein-protein interactions and determines substrate and extracellular matrix (ECM) binding [17]. Furthermore, the $\beta$ propeller is involved in forming supra-molecular complexes of FAP with other prolyl peptidases or with other membrane-bound molecules [18, 19]. The formation of heteromeric or tetrameric complexes of FAP and DPPIV were found to be associated with invadopodia of migrating cells on a collagen substrate [20]. Type I collagen induces a close association of FAP with $\beta1$ integrins, thereby playing major organizational roles in the formation and adhesion of invadopodia [21]. Although the involved mechanisms are not understood in detail, the formation of such proteinase-rich membrane domains at the cellular invasion front contributes to directed pericellular ECM degradation [22]. This indicates that FAP and ECM interactions may be closely related to invasive cell behaviour by influencing cell adhesion, migration, proliferation and apoptosis through integrin pathways [19, 21, 23] and supports o role of FAP in disease pathogenesis and progression [24]. In summary, FAP is recognized as a multifunctional protein that executes its biological functions in a cell dependent manner through a combination of its protease activity and its ability to form complexes with other cell-surface molecules. Over-expression of FAP in epithelial and fibroblastic cell lines promotes malignant behaviour [22], pointing to the clinical situation, where cellular expression levels of FAP are correlated with worse clinical outcome [25, 26].

Through paracrine signaling molecules, cancer cells activate stromal fibroblasts and induce the expression of FAP, which in turn, affects the proliferation, invasion and migration of the cancer cells. Recent studies have demonstrated that TGF-$\beta$ is the dominant factor in promoting FAP protein expression (Chen, H et al (2009) Exp and Molec Pathology, doi: 10.1016/j.yexmp. 2009.09.001). FAP is heavily expressed on reactive stromal fibroblasts in 90% of human epithelial carcinomas, including those of the breast, lung, colorectum and ovary (Garin-Chesa, P et al (1990) PNAS USA 87: 7236-7239). Chen et al have recently shown that FAPα influences the invasion, proliferation and migration of HO-8910PM ovarian cancer cells (Chen, H et al (2009) Exp and Molec Pathology, doi: 10.1016/j.yexmp. 2009.09.001).

The morphological and functional properties of FAP promote the investigation of FAP as a therapeutic target. The disease related and cell surface bound expression pattern especially qualifies FAP for antibody targeting. With regard to the pathophysiological involvement in ECM remodelling, targeting strategies should aim at the disruption of the signalling supra-molecular FAP complexes. Although FAP has attracted increased interest as a target for antibody based immunotherapy, data of therapeutically active native FAP-specific antibodies are missing to date. The monoclonal antibody F19 was the first antibody investigated in a phase I clinical trial targeting metastatic colorectal cancer [30]. This trial served as a proof of principle for anti-FAP based tumor stroma targeting [1]. Although patients included in the trial had extensive scarring due to surgery, no specific enrichment of [131]I-F19 could be detected at these sites. There were no toxic side effects associated with intravenous administration of iodine[131] labelled F19 and carcinoma lesions were specifically detected by imaging down to a size of 1 cm in diameter. With regard to the immunogenicity of murine antibodies in humans, recent phase I and phase II clinical trials were conducted using the humanized version of F19, called Sibrotuzumab [31, 32]. Results from these trials demonstrated the safe and well tolerated administration of Sibrotuzumab. Similar to the results obtained in the pivotal phase I trial [30], trace-labelling with $^{131}$I and imaging analysis revealed the specific accumulation of Sibrotuzumab at the tumor area. Unfortunately, unconjugated Sibrotuzumab demonstrated no anti-tumor or any therapeutic activity, respectively [32]. Although the biologic function of FAP is still not known in detail, its dipeptidyl peptidase activity was postulated to be involved in tumor progression and metastasis [15, 33]. The lack of Sibrotuzumab to affect FAP enzymatic function was suggested to be the reason for the lack of therapeutic efficacy [34]. In consequence, anti-FAP directed polyclonal antibodies have been raised in order to inhibit the catalytic activity in-vitro. Indeed, treatment of FAP-positive xenografts with anti-FAP anti-sera attenuated tumor growth [13]. However, since polyclonal sera were raised by immunization of rabbits with murine FAP, it is most likely that additional epitopes, different from the catalytic domain, have also been targeted. Therefore, it is difficult to conclude from this study that anti-tumor effects seen really depended on dipeptidyl-peptidase inhibition.

Thus, while the extant evidence of activity of FAP antibodies is encouraging, the observed limitations on efficacy and anti-tumor activity remain. Accordingly, it would be desirable to develop FAP antibodies, particularly antibodies which can be utilized in mouse animal models and which demonstrate increased efficacy and applicability in diagnosis and therapy, and it is toward the achievement of that objective that the present invention is directed.

The citation of references herein shall not be construed as an admission that such is prior art to the present invention.

SUMMARY OF THE INVENTION

The invention provides antibodies directed against Fibroblast activation protein (FAP) for diagnostic and therapeutic purposes. In particular, antibodies specific for FAP are provided, wherein said antibodies recognize and are capable of binding human and mouse FAP. Fab antibodies are particularly provided herein. The antibodies of the present invention have diagnostic and therapeutic use in conditions associated with activated stroma, including wound healing, epithelial cancers, osteoarthritis, rheumatoid arthritis, cirrhosis and pulmonary fibrosis and FAP positive tumors such as pancreatic cancer, melanoma and different sarcomas. In a particular aspect the antibodies of the invention are applicable in cancers, including epithelial cancers, including breast, lung, colorectal and ovarian cancers.

In a general aspect, the present invention provides FAP antibodies directed against human and mouse FAP and which do not cross react/bind to CD26 (dipeptidyl peptidase IV (DPPIV)). In a broad aspect, the present invention provides an isolated specific binding member, particularly an antibody or fragment thereof, including a Fab fragment and a single chain or domain antibody, which recognizes human FAP. In a further aspect, the present invention provides an antibody or fragment thereof, which recognizes human FAP and comprises the amino acid sequence of ESC11 or ESC14 including as set out in FIG. 2 and/or FIG. 10. In one such aspect, the invention provides an anti-human FAP antibody comprising the variable region CDR sequences set out in FIG. 10.

In a particular aspect, the antibody or fragment of the invention is reactive with, capable of binding human and mouse FAP. In a further aspect the antibody or fragment does not react with, does not bind to CD26 (DPPIV). In an aspect, binding of the antibody or fragment of the invention does not directly affect dipeptidyl peptidase activity. In an additional aspect, the antibody or fragment down regulates the expression of FAP and therefore reduces the number or amount of active dipetidyl peptidase enzyme activity on a cells surface. By reducing FAP expression on the cell surface, the antibody(ies) of the invention indirectly impact on dipeptidyl peptidase activity. In a still further aspect, the antibody or fragment mediates down regulation of FAP expression. In another aspect the antibody or fragment induces, mediates apoptosis in FAP expressing cells. In a still additional aspect the antibody or fragment inhibits cellular adhesion to ECM proteins. Thus, the anti-FAP antibody(ies) or active fragment(s) thereof of the invention has at least two of the following characteristics: is reactive with human and mouse FAP; does not react with or bind to CD26 (DPPIV); does not directly affect dipeptidyl peptidase activity of FAP; mediates down regulation of FAP expression; induces or otherwise mediates apoptosis in FAP expressing cells; and inhibits cellular adhesion to ECM proteins.

The present inventors have discovered novel FAP antibodies which are reactive to human and mouse FAP and do not react with CD26. The antibodies exemplified herein include Fab antibodies and recombinant antibodies based thereon. Exemplary antibodies provided include ESC11 and ESC14. The antibodies have the heavy and light chain variable region sequences and comprise CDR domain region sequences as set out herein and in FIGS. 2 and 10.

The unique specificity and affinity of the antibodies and fragments of the invention provides diagnostic and therapeutic uses to identify, characterize and target conditions associated with activated stroma, including wound healing, epithelial cancers, osteoarthritis, rheumatoid arthritis, cirrhosis and pulmonary fibrosis, particularly without the problems associated with normal tissue uptake. Cancers whose progression, migration and/or invasion involves, is facilitated by, or is associated with stromal fibroblasts are particularly susceptible to and targeted by the antibodies of the present invention. Such cancers include epithelial cancers, including breast, lung, colorectal and ovarian cancer.

In a preferred aspect, the antibody is one which has the characteristics of the antibodies which the inventors have identified and characterized, in particular recognizing human and mouse FAP and not recognizing related protein CD26. In a particularly preferred aspect the antibody is ESC11 or ESC14, or active fragments thereof. In a further preferred aspect the antibody of the present invention comprises the VH and VL amino acid sequences depicted in FIGS. 2 and 10 (VH sequences SEQ ID NO: 1, SEQ ID NO: 2, SEQ ID NO: 7, and VL sequences SEQ ID NO: 3, SEQ ID NO: 8). In a particular aspect, the antibody of the invention comprises the CDR sequences depicted in FIG. 10. In a particular aspect of the invention the antibody is ESC11 and comprises the variable region sequences set out in FIG. 2 or FIG. 10 (VH sequence SEQ ID NO: 1 or 2, and VL sequence SEQ ID NO: 3). In a particular aspect of the invention the antibody is ESC11 and comprises the CDR region sequences set out in FIG. 10 (heavy chain CDR 1 (SEQ ID NO: 11), CDR2 (SEQ ID NO: 12), CDR3 (SEQ ID NO: 13); light chain CDR 1 (SEQ ID NO: 17), CDR2 (SEQ ID NO: 18), CDR3 (SEQ ID NO: 19)). In a particular aspect of the invention the antibody is ESC14 and comprises the variable region sequences set out in FIG. 2 or FIG. 10 (VH sequence SEQ ID NO: 7, and VL sequence SEQ ID NO: 8). In a particular aspect of the invention the antibody is ESC14 and comprises the CDR region sequences set out in FIG. 10 (heavy chain CDR 1 (SEQ ID NO: 14), CDR2 (SEQ ID NO: 15), CDR3 (SEQ ID NO: 16); light chain CDR 1 (SEQ ID NO: 20), CDR2 (SEQ ID NO: 21), CDR3 (SEQ ID NO: 22)).

The binding of an antibody to its target antigen is mediated through the complementarity-determining regions (CDRs) of its heavy and light chains. Accordingly, specific binding members based on the CDR regions of the heavy or light chain, and preferably both, of the antibodies of the invention, particularly of ESC11 and/or ESC14, will be useful specific binding members for therapy and/or diagnostics. The sequences and CDRs of the antibodies are depicted in FIGS. 2 and 10. FIG. 2A depicts the ESC11 antibody heavy and light chain DNA sequences and amino acid sequences. The ESC11 heavy chain variable region amino acid sequence is set out in SEQ ID NO:1, and the heavy chain peptide sequence modified for eukaryotic expression is set out in SEQ ID NO:2. Nucleic acid sequence encoding these heavy chain peptide sequences are set out in SEQ ID NOS: 4 and 5 respectively. The ESC11 light chain amino acid sequence corresponds to SEQ ID NO: 3, and the encoding DNA sequence to SEQ ID NO: 6. FIG. 2B depicts the ESC14 antibody heavy and light chain DNA sequences and amino acid sequences. The ESC14 heavy chain variable region amino acid sequence is set out in SEQ ID NO:7. Nucleic acid sequence encoding this heavy chain peptide sequence corresponds to SEQ ID NO: 9. The ESC14 light chain amino acid sequence corresponds to SEQ ID NO: 8, and the encoding DNA sequence to SEQ ID NO: 10. The ESC11 antibody heavy chain Antibody ESC11 comprises heavy chain CDR sequences GGSISSNNYYWG (SEQ ID NO: 11), SIYYSGSTNYNPSLKS (SEQ ID NO: 12) and GARWQARPATRIDGVAFDI (SEQ ID NO: 13), and light chain CDR sequences RASQTVTRNYLA (SEQ ID NO: 17), GASNRAA (SEQ ID NO: 18) and QQFGSPYT (SEQ ID NO:19), as set out in FIG. 10. Antibody ESC14 comprises heavy chain CDR sequences GYTFTSYGIS (SEQ ID NO: 14), WISAYNGNTNYAQKLQG (SEQ ID NO: 15) and DWSRSGYYLPDY (SEQ ID NO: 16) and light chain CDR sequences RSSQ SLLHSNGYNYLD (SEQ ID NO: 20), LGSNRAS (SEQ ID NO: 21) and MQALQTPPT (SEQ ID NO: 22), as set out in FIG. 10. Core CDR sequences based on the homology and similarity of the ESC and ESC14 antibody CDR sequences include for the heavy chain, CDR I of G G/Y S/T I/F S/T S N/– N/– Y Y/G W/I G/S, CDRII of S/W I S/– Y/A Y S/N G S/N T N Y N/A P/Q S/K L K/Q S/G, and CDRIII of G/D A/– R/– W Q/– A/– R/– P/– A/– T/S R I/S D/G G/Y V/Y A/L F/P D I/Y. Core CDR sequences based on the homology and similarity of the ESC11 and ESC14 antibody CDR sequences include for the light chain, CDR I of R A/S S Q T/S V/L T/L R/H S/– N/– G/– Y/– N Y L A/D, CDRII of G/L A/G SNRA A/S, and CDRIII of Q/M Q A/– F/L G/Q S/T P Y/P T.

Accordingly, specific binding proteins such as antibodies which are based on the CDRs of the antibody(ies) identified herein will be useful for targeting stroma, particularly FAP and FAP expressing cells in diseases or in cancers. As the FAP target of the antibodies of the invention is not significantly expressed in normal cells or normal stromal fibroblasts the antibodies of the invention do no significantly bind to normal somatic cells, it is anticipated that there will not be significant uptake in normal tissue and there will be suitable and specific affinity for the FAP target.

In a further aspect, the present invention provides an isolated antibody or fragment thereof capable of binding an antigen, wherein said antibody or fragment thereof comprises a polypeptide binding domain comprising an amino acid sequence substantially as set out herein and in FIG. 10.

In further aspects, the invention provides an isolated nucleic acid which comprises a sequence encoding a specific binding member as defined above, and methods of preparing specific binding members of the invention which comprise expressing said nucleic acids under conditions to bring about expression of said binding member, and recovering the binding member. In one such aspect, a nucleic acid encoding antibody variable region sequence having the amino acid sequences as set out in FIG. 2 or 10 is provided or an antibody having CDR domain sequences as set out in FIG. 10 is provided. In one aspect, a nucleic acid of FIG. 2 is provided. The present invention also relates to a recombinant DNA molecule or cloned gene, or a degenerate variant thereof, which encodes an antibody of the present invention; preferably a nucleic acid molecule, in particular a recombinant DNA molecule or cloned gene, encoding the antibody VH and VL, particularly the CDR region sequences, which has a sequence or is capable of encoding a sequence shown in FIG. 2 or 10.

The antibodies, fragments thereof and recombinant antibodies comprising the CDR domains according to the invention may be used in a method of treatment or diagnosis of the human or animal body, such as a method of treatment of a tumor in a human patient which comprises administering to said patient an effective amount of the antibodies, fragments thereof and recombinant antibodies of the invention.

The present invention also includes polypeptides or antibodies having the activities noted herein, and that display the amino acid sequences set forth and described above and in FIG. 2 or 10 hereof, or are antibodies having a heavy chain and a light chain wherein the complementarity determining regions (CDRs) of the heavy and light chain comprise the amino acid sequences depicted in each or any of FIGS. 2 and 10.

The diagnostic utility of the present invention extends to the use of the antibodies of the present invention in assays to characterize tumors or cellular samples or to screen for tumors or cancer, including in vitro and in vivo diagnostic assays. In an immunoassay, a control quantity of the antibodies, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

Specific binding members of the invention may carry a detectable or functional label. The specific binding members may carry a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{121}$I, $^{124}$I, $^{125}$I, $^{131}$I, $^{111}$In, $^{117}$Lu, $^{211}$At, $^{198}$Au, $^{67}$Cu, $^{225}$Ac, $^{213}$Bi, $^{99}$Tc and $^{186}$Re. When radioactive labels are used, known currently available counting procedures may be utilized to identify and quantitate the specific binding members. In the instance where the label is an enzyme, detection may be accomplished by any of the presently utilized colorimetric, spectrophotometric, fluorospectrophotometric, amperometric or gasometric techniques known in the art.

The radiolabelled specific binding members, particularly antibodies and fragments thereof, are useful in in vitro diagnostics techniques and in in vivo radioimaging techniques. In a further aspect of the invention, radiolabelled specific binding members, particularly antibodies and fragments thereof, particularly radioimmunoconjugates, are useful in radioimmunotherapy, particularly as radiolabelled antibodies for cancer therapy. In a still further aspect, the radiolabelled specific binding members, particularly antibodies and fragments thereof, are useful in radioimmuno-guided surgery techniques, wherein they can identify and indicate the presence and/or location of cancer cells, precancerous cells, tumor cells, and hyperproliferative cells, prior to, during or following surgery to remove such cells.

Immunoconjugates or antibody fusion proteins of the present invention, wherein the specific binding members, particularly antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

The present invention includes an assay system which may be prepared in the form of a test kit for the quantitative analysis of the extent of the presence of, for instance, FAP. The system or test kit may comprise a labeled component prepared by one of the radioactive and/or enzymatic techniques discussed herein, coupling a label to the antibody, and one or more additional immunochemical reagents, at least one of which is a free or immobilized components to be determined or their binding partner(s).

In a further embodiment, the present invention relates to certain therapeutic methods which would be based upon the activity of the binding member, antibody, or active fragments thereof, or upon agents or other drugs determined to possess the same activity. A first therapeutic method is associated with the prevention or treatment of cancer, including but not limited to melanoma, lung, esophageal, liver, gastric, prostate, ovarian, bladder and synovial sarcoma.

The binding members and antibodies of the present invention, and in a particular embodiment the antibody whose sequences are presented in FIGS. 2 and 10 herein, or active fragments thereof, and single chain, recombinant or synthetic antibodies derived therefrom, particularly comprising the CDR region sequences depicted in FIG. 10, can be prepared in pharmaceutical compositions, including a suitable vehicle, carrier or diluent, for administration in instances wherein therapy is appropriate, such as to treat cancer. Such pharmaceutical compositions may also include methods of modulating the half-life of the binding members, antibodies or fragments by methods known in the art such as pegylation. Such pharmaceutical compositions may further comprise additional antibodies or therapeutic agents.

A composition of the present invention may be administered alone or in combination with other treatments, therapeutics or agents, either simultaneously or sequentially dependent upon the condition to be treated. In addition, the present invention contemplates and includes compositions comprising the binding member, particularly antibody or fragment thereof, herein described and other agents or therapeutics such as anti-cancer agents or therapeutics, anti-mitotic agents, apoptotic agents or antibodies, or immune modulators. More generally these anti-cancer agents may be tyrosine kinase inhibitors or phosphorylation cascade inhibitors, post-translational modulators, cell growth or division inhibitors (e.g. anti-mitotics), inhibitors or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. In addition, the composition may be administered with immune modulators, such as interleukins, tumor necrosis factor (TNF) or other growth factors, colony stimulating factors, cytokines or hormones such as dexamethasone which stimulate the immune response and reduction or elimination of cancer cells or tumors. The composition may also be administered with, or may include combinations along with other anti-FAP antibodies or other anti-tunor antigen antibodies.

The present invention also includes antibodies and fragments thereof, which are covalently attached to or otherwise associated with other molecules or agents. These other molecules or agents include, but are not limited to, molecules (including antibodies or antibody fragments) with distinct recognition characteristics, toxins, ligands, and chemotherapeutic agents. In an additional aspect the antibodies or fragments of the invention may be used to target or direct therapeutic molecules or other agents, for example to target molecules or agents to FAP expressing cells, for example to stromal cells or activated stromal cells at wound sites, tumor sites, inflammatory areas or cancerous lesions.

Other objects and advantages will become apparent to those skilled in the art from a review of the ensuing detailed description, which proceeds with reference to the following illustrative drawings, and the attendant claims.

BRIEF DESCRIPTION OF THE DRAWINGS

FIGS. 2A and 2B: ESC11 (A) and ESC14 (B) antibody sequences. The DNA sequences of heavy and light chains of both antibodies are depicted. ESC11 heavy and light chain DNA sequences correspond to SEQ ID NO: 4 or 5 and SEQ ID NO: 6 respectively. ESC 14 heavy and light chain DNA sequences correspond to SEQ ID NO: 9 and SEQ ID NO: 10 respectively. The heavy chain amino acid sequence of ESC11 (SEQ ID NO: 1) was mutated (highlighted in red) from Histidine (H) to Glutamine (Q) at amino-acid position I to allow for expression in eukaryotic cells (SEQ ID NO: 2). The light chain peptide sequence of ESC11 coresponds to SEQ ID NO: 3. The heavy chain amino acid sequence of ESC 14 corresponds to SEQ ID NO: 7 and the light chain to SEQ ID NO: 8.

FIGS. 10A and B depicts an alignment of the ESC11 and ESC14 antibody variable region Heavy chain (A) and Light chain (B) sequences. The CDR I, II and III region sequences are highlighted. Heavy chain CDR I, II and III of ESC11 correspond to SEQ ID. NOS: 11, 12 and 13, and light chain CDR I, II and II to SEQ ID NO: 17, 18 and 19. Heavy chain CDR I, II and III of ESC 14 correspond to SEQ ID NOS: 14, 15 and 16, and light chain CDR I, II and II to SEQ ID NO: 20, 21 and 22. Identical amino acids are noted, conserved amino acids are shown as a +, and gaps in the sequence are noted as dashes (−).

FIGS. 11A, B and C depicts fluorescence microscopy of HT 1080 FAP cells treated with Dy Light 488 (Thermo Scientific) labeled ESC11 IgG. (A) shows incubation at 4° C. and membrane staining with ESC11 IgG$^{in}$ (B) cells were warmed to 37° C. for 4 hours. Internalization of FAP-ESC11 complexes is detected with cytoplasmic spots and vesicular accumulation. The ESC11 IgG incubated cells were held at 37° C. for 2 hours and then washed with acid in (C). Internalized FAP-antibody complex is seen in (C) demonstrating that most of the antibody had internalized in the 2 hours of incubation.

DETAILED DESCRIPTION

Figure 1:
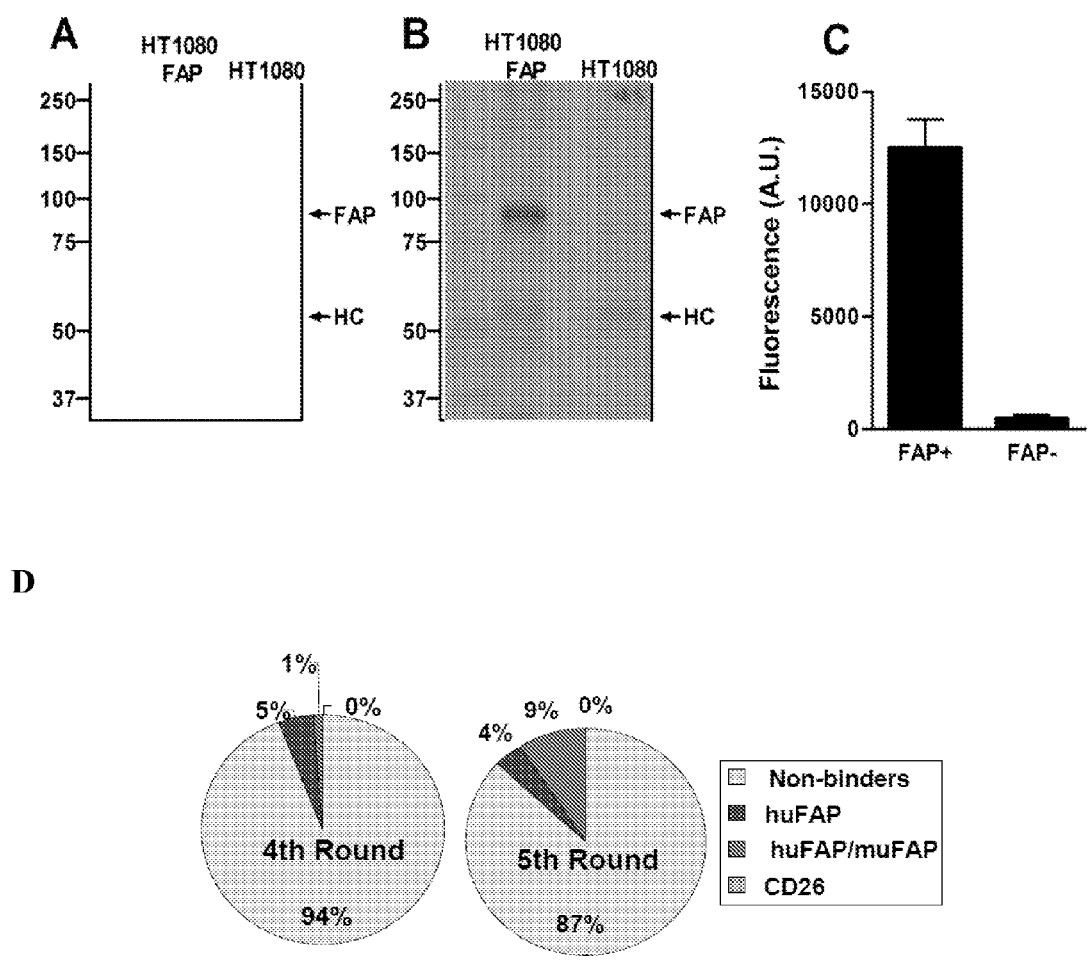
FIG. 1A-1D: Selection of Fab-fragments and immunoprecipitation of recombinant FAP. A. Coomassie blue stained SDS-PAGE gel and B. Corresponding western blot probed with F19 antibody. C. Dipeptidyl-peptidase activity in immunocaptured FAP from HT1080 FAP$^+$ lysates (FAP+) and the mock immunocapture from HT1080 lysates (FAP-). A.U., arbitrary units. HC, heavy chain. D. Reactivity pattern of selected phages on different target antigens after 4 and 5 rounds of selection.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A. Terminology

The term "specific binding member" describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

The term "antibody" describes an immunoglobulin whether natural or partly or wholly synthetically produced. The term also covers any polypeptide or protein having a binding domain which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Also included within the meaning of the term "antibody" are any "antibody fragment".

An "antibody fragment" means a molecule comprising at least one polypeptide chain that is not full length, including (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region; (iii) a heavy chain portion of an Fab (Fd) fragment, which consists of the VH and CH1 domains; (iv) a variable fragment (Fv) fragment, which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1-VH-CH1) which, together with complementarity light chain polypeptides, form a pair of antigen binding regions; (xi) multivalent antibody fragments (scFv dimers, trimers and/or tetramers (Power and Hudson, J. Immunol. Methods 242: 193-204 9 (2000)); and (xii) other non-full length portions of heavy and/or light chains, or mutants, variants, or derivatives thereof, alone or in any combination.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

An "antibody combining site" is that structural portion of an antibody molecule comprised of light chain or heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-cancer or anti-tumor specific antibody. The other binding domain may be an antibody that recognizes or targets a particular cell type, as in a neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine (e.g. tumor necrosis factor (TNF), and particularly, the TNF bispecific modality demonstrated in U.S. Ser. No. 60/355,838 filed Feb. 13, 2002 incorporated herein in its entirety) or a toxin (e.g., ricin) or anti-mitotic or apoptotic agent or factor. Thus, the anti-FAP antibodies of the invention may be utilized to direct or target agents, labels, other molecules or compounds or antibodies to stromal sites, particular areas of wound healing, inflammation, cancer or tumors.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may also contain an antibody molecule having a plurality of antibody combining sites, each immunospecific for a different antigen; e.g., a bispecific (chimeric) monoclonal antibody.

The term "antigen binding domain" describes the part of an antibody which comprises the area which specifically binds to and is complementary to part or all of an antigen. Where an antigen is large, an antibody may bind to a particular part of the antigen only, which part is termed an epitope. An antigen binding domain may be provided by one or more antibody variable domains. Preferably, an antigen binding domain comprises an antibody light chain variable region (VL) and an antibody heavy chain variable region (VH).

Immunoconjugates or antibody fusion proteins of the present invention, wherein the antibodies, antibody molecules, or fragments thereof, of use in the present invention are conjugated or attached to other molecules or agents further include, but are not limited to such antibodies, molecules, or fragments conjugated to a chemical ablation agent, toxin, immunomodulator, cytokine, cytotoxic agent, chemotherapeutic agent, antimicrobial agent or peptide, cell wall and/or cell membrane disrupter, or drug.

The term "specific" may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "comprise" generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which specific binding members of the invention, or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy.

As used herein, "pg" means picogram, "ng" means nanogram, "ug" or "µg" mean microgram, "mg" means milligram, "ul" or "µl" mean microliter, "ml" means milliliter, "l" means liter.

The terms "antibody", "nati-FAP antibody", "FAP antibody", "human/mouse FAP antibody", "antibody ESC11", "antibody ESC14" and any variants not specifically listed, may be used herein interchangeably, and as used throughout the present application and claims refer to proteinaceous material including single or multiple proteins, and extends to those proteins having the amino acid sequence data described herein and presented in FIGS. 2 and 10 and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "antibody", "nati-FAP antibody", "FAP antibody", "human/mouse FAP antibody", "antibody ESC11", "antibody ESC14" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired fuctional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alis, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding specific binding members (antibodies) of the invention which code for e.g. an antibody having the same amino acid sequence as provided in FIG. 2 or 10, or comprising the CDR domain region sequences set out herein or in FIG. 10 but which are degenerate thereto. By "degenerate to" is meant that a different three-letter codon is used to specify a particular amino acid. It is well known in the art that the following codons can be used interchangeably to code for each specific amino acid:

```
Phenylalanine (Phe or F)  UUU or UUC

Leucine (Leu or L)        UUA or UUG or CUU or CUC or CUA or CUG

Isoleucine (Ile or I)     AUU or AUC or AUA

Methionine (Met or M)     AUG

Valine (Val or V)         GUU or GUC of GUA or GUG

Serine (Ser or S)         UCU or UCC or UCA or UCG or AGU or AGC

Proline (Pro or P)        CCU or CCC or CCA or CCG

Threonine (Thr or T)      ACU or ACC or ACA or ACG

Alanine (Ala or A)        GCU or GCG or GCA or GCG

Tyrosine (Tyr or Y)       UAU or UAC

Histidine (His or H)      CAU or CAC

Glutamine (Gln or Q)      CAA or CAG

Asparagine (Asn or N)     AAU or AAC

Lysine (Lys or K)         AAA or AAG

Aspartic Acid (Asp or D)  GAU or GAC

Glutamic Acid (Glu or E)  GAA or GAG
```

```
Cysteine (Cys or C)        UGU or UGC
                            -continued Arginine (Arg or R)        CGU or CGC or CGA or CGG or AGA or AGG Glycine (Gly or G)         GGU or GGC or GGA or GGG Tryptophan (Trp or W)      UGG Termination codon          UAA (ochre) or UAG (amber) or UGA (opal)
```

It should be understood that the codons specified above are for RNA sequences. The corresponding codons for DNA have a T substituted for U.

Mutations can be made in the sequences encoding the amino acids, antibody fragments, CDR region sequences set out in FIG. 2 or 10, or in the sequence of FIG. 10, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (for example, by changing the codon from an amino acid belonging to a grouping of amino acids having a particular size or characteristic to an amino acid belonging to another grouping) or in a conservative manner (for example, by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:
Amino Acids with Nonpolar R Groups
Alanine, Valine, Leucine, Isoleucine, Proline, Phenylalanine, Tryptophan, Methionine
Amino Acids with Uncharged Polar R Groups
Glycine, Serine, Threonine, Cysteine, Tyrosine, Asparagine, Glutamine
Amino Acids with Charged Polar R Groups (Negatively Charged at pH 6.0)
Aspartic acid, Glutamic acid
Basic Amino Acids (Positively Charged at pH 6.0)
Lysine, Arginine, Histidine (at pH 6.0)
Another grouping may be those amino acids with phenyl groups:
Phenylalanine, Tryptophan, Tyrosine
Another grouping may be according to molecular weight (i.e., size of R groups):

| Glycine | 75 | Alanine | 89 |
|---|---|---|---|
| Serine | 105 | Proline | 115 |
| Valine | 117 | Threonine | 119 |
| Cysteine | 121 | Leucine | 131 |
| Isoleucine | 131 | Asparagine | 132 |
| Aspartic acid | 133 | Glutamine | 146 |
| Lysine | 146 | Glutamic acid | 147 |
| Methionine | 149 | Histidine (at pH 6.0) | 155 |
| Phenylalanine | 165 | Arginine | 174 |
| Tyrosine | 181 | Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Exemplary and preferred conservative amino acid substitutions include any of: glutamine (Q) for glutamic acid (E) and vice versa; leucine (L) for valine (V) and vice versa; serine (S) for threonine (T) and vice versa; isoleucine (I) for valine (V) and vice versa; lysine (K) for glutamine (Q) and vice versa; isoleucine (I) for methionine (M) and vice versa; serine (S) for asparagine (N) and vice versa; leucine (L) for methionine (M) and vice versa; lysine (L) for glutamic acid (E) and vice versa; alanine (A) for serine (S) and vice versa; tyrosine (Y) for phenylalanine (F) and vice versa; glutamic acid (E) for aspartic acid (D) and vice versa; leucine (L) for isoleucine (I) and vice versa; lysine (K) for arginine (R) and vice versa.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions. The CDR regions of two antibodies are substantially homologous when one or mre amino acids are substituted with a similar or conservative amino acid substitution, and wherein the antibody/antibodies have the profile of binding and activities of one or more of ESC11 or ESC14 disclosed herein.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

The term 'agent' means any molecule, including polypeptides, antibodies, polynucleotides, chemical compounds and small molecules. In particular the term agent includes compounds such as test compounds or drug candidate compounds.

The term 'agonist' refers to a ligand that stimulates the receptor the ligand binds to in the broadest sense.

The term 'assay' means any process used to measure a specific property of a compound. A 'screening assay' means a process used to characterize or select compounds based upon their activity from a collection of compounds.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Therapeutically effective amount' means that amount of a drug, compound, antimicrobial, antibody, or pharmaceutical agent that will elicit the biological or medical response of a subject that is being sought by a medical doctor or other clinician. In particular, with regard to gram-positive bacterial infections and growth of gram-positive bacteria, the term "effective amount" is intended to include an effective amount of a compound or agent that will bring about a biologically meaningful decrease in the amount of or extent of infection of gram-positive bacteria, including having a bacteriocidal and/or bacteriostatic effect. The phrase "therapeutically effective amount" is used herein to mean an amount sufficient to prevent, and preferably reduce by at least about 30 percent, more preferably by at least 50 percent, most preferably by at least 90 percent, a clinically significant change in the growth or amount of infectious bacteria, or other feature of pathology such as for example, elevated fever or white cell count as may attend its presence and activity.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease or reducing an infection.

The phrase "pharmaceutically acceptable" refers to molecular entities and compositions that are physiologically tolerable and do not typically produce an allergic or similar untoward reaction, such as gastric upset, dizziness and the like, when administered to a human.

As used herein, "pg" means picogram, "ng" means nanogram, "ug" or "µg" mean microgram, "mg" means milligram, "ul" or "µl" mean microliter, "ml" means milliliter, "l" means liter.

B. Detailed Disclosure

The invention provides antibodies directed against Fibroblast activation protein (FAP) for diagnostic and therapeutic purposes. In particular, antibodies specific for FAP are provided, wherein said antibodies recognize and are capable of binding human and mouse FAP. Fab antibodies are particularly provided herein. The antibodies of the present invention have diagnostic and therapeutic use in conditions associated with activated stroma, including wound healing, epithelial cancers, osteoarthritis, rheumatoid arthritis, cirrhosis and pulmonary fibrosis. In a particular aspect the antibodies of the invention are applicable in cancers, including epithelial cancers, including breast, lung, colorectal and ovarian cancers.

In a general aspect, the present invention provides FAP antibodies directed against human and mouse FAP and which do not cross react/bind to CD26 (dipeptidyl peptidase IV (DPPIV)). In a broad aspect, the present invention provides an isolated specific binding member, particularly an antibody or fragment thereof, including an Fab fragment and a single chain or domain antibody, which recognizes human FAP. In a further aspect, the present invention provides an antibody or fragment thereof, which recognizes human FAP and comprises the amino acid sequence of ESC11 or ESC14 including as set out in FIG. 2 and/or FIG. 10. In one such aspect, the invention provides an anti-human FAP antibody comprising the variable region CDR sequences set out in FIG. 10.

In a particular aspect, the antibody or fragment of the invention is reactive with, capable of binding human and mouse FAP. In a further aspect the antibody or fragment does not react with, does not bind to CD26 (DPPIV). In an additional aspect, the antibody or fragment does not directly effect dipeptidyl peptidase activity of FAP. In a still further aspect, the antibody or fragment mediates down regulation of FAP expression. In another aspect the antibody or fragment induces, mediates apoptosis in FAP expressing cells. In a still additional aspect the antibody or fragment inhibits cellular adhesion to ECM proteins. Thus, the anti-FAP antibody(ies) or active fragment(s) thereof of the invention has at least two of the following characteristics: is reactive with human and mouse FAP; does not react with or bind to CD26 (DPPIV); does not directly affect dipeptidyl peptidase activity of FAP; mediates down regulation of FAP expression; induces or otherwise mediates apoptosis in FAP expressing cells; and inhibits cellular adhesion to ECM proteins.

Panels of monoclonal antibodies recognizing human and murine FAP can be screened for various properties; i.e., isotype, epitope, affinity, etc. Of particular interest are antibodies that mimic the activity of exemplary antibodies ESC11 and ESC14, and have affinity for human and mouse FAP, do not react with CD26, and do not directly effect the dipeptidyl peptidase activity of FAP. Such antibodies can be readily identified and/or screened in specific binding member activity assays.

In general, the CDR regions, comprising amino acid sequences substantially as set out as the CDR regions of FIG. 10 will be carried in a structure which allows for binding of the CDR regions to the stromal protein FAP, and particularly to human and mouse FAP.

By "substantially as set out" it is meant that that variable region sequences, and/or particularly the CDR sequences, of the invention will be either identical or highly homologous to the specified regions of FIG. 10. By "highly homologous" it is contemplated that only a few substitutions, preferably from 1 to 8, preferably from 1 to 5, preferably from 1 to 4, or from 1 to 3, or 1 or 2 substitutions may be made in the variable region sequence and/or in the CDR sequences. The term substantuially set out as includes particularly conservative amino acid substitutions which do not materially or significantly affect the specificity and/or activity of the instant antibodies. Conservative amino acid substitutions are exemplified herein and also in FIG. 10 for the CDR region sequences.

Substitutions may be made in the variable region sequence outside of the CDRs so as to retain the CDR sequences. Thus, changes in the variable region sequence or alternative non-homologous or veneered variable region sequences may be introduced or utilized, such that the CDR sequences are maintained and the remainder of the variable region sesuence may be substituted.

Alternatively, substitutions may be made particularly in the CDRs. CDR sequences for the antibodies of the present invention are set out and described herein including in FIG. 10. Antibody ESC11 comprises heavy chain CDR sequences GGSISSNNYYWG (SEQ ID NO: 11), SIYYSGSTNYNPSLKS (SEQ ID NO: 12) and GARWQARPATRIDGVAFDI (SEQ ID NO: 13), and light chain CDR sequences RASQTVTRNYLA (SEQ ID NO: 17), GASNRAA (SEQ ID NO: 18) and QQFGSPYT (SEQ ID NO: 19), as set out in FIG. 10. Antibody ESC14 comprises heavy chain CDR sequences GYTFTSYGIS (SEQ ID NO: 14), WISAYNGNTNYAQKLQG (SEQ ID NO: 15) and DWSRSGYYLPDY (SEQ ID NO: 16) and light chain CDR sequences RSSQSLLHSNGYNYLD (SEQ ID NO: 20), LGSNRAS (SEQ ID NO: 21) and MQALQTPPT (SEQ ID NO: 22), as set out in FIG. 10. Core CDR sequences based on the homology and similarity of the ESC11 and ESC14 antibody CDR sequences include for the heavy chain, CDR I of G G/Y S/T I/F S/T S N/– N/– Y Y/G W/I G/S, CDR11 of S/W I S/– Y/A Y S/N G S/N T NY N/A P/Q S/K L K/Q S/G, and CDRIII of G/D A/– R/– W Q/– A/– R/– P/– A/– T/S R I/S D/G G/Y V/Y A/L F/P D I/Y. Core CDR sequences based on the homology and similarity of the ESC11 and ESC14 antibody CDR sequences include for the light chain, CDR I of R A/S S Q T/S V/L T/L R/H S/– N/– G/– Y/– NY L A/D, CDRII of G/L A/G SNR A A/S, and CDRIII of Q/M Q A/– F/L G/Q S/T P Y/P T.

Antibodies of the invention having substitutions as above described and contemplated are selected to maintain the activities and specifity commensurate with the exemplary antibodies, including antibodies ESC11 and ESC14 and having the characteristics as set out herein and in the claims.

The structure for carrying the CDRs of the invention will generally be of an antibody heavy or light chain sequence or substantial portion thereof in which the CDR regions are located at locations corresponding to the CDR region of naturally occurring VH and VL antibody variable domains encoded by rearranged immunoglobulin genes. The structures and locations of immunoglobulin variable domains may be determined by reference to Kabat, E. A. et al, Sequences of Proteins of Immunological Interest. 4th Edition. US Department of Health and Human Services. 1987, and updates thereof, now available on the Internet (http://immuno.bme.nwu.edu)).

The variable domains may be derived from any germline or rearranged human variable domain, or may be a synthetic variable domain based on consensus sequences of known human variable domains. The CDR-derived sequences of the invention, as defined in the preceding paragraph, may be introduced into a repertoire of variable domains lacking CDR regions, using recombinant DNA technology.

For example, Marks et al (Bio/Technology, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR/CDRs. Marks et al further describe how this repertoire may be combined with a CDR of a particular antibody. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members. Analogous shuffling or combinatorial techniques are also disclosed by Stemmer (Nature, 1994, 370:389-391), who describes the technique in relation to a β-lactamase gene but observes that the approach may be used for the generation of antibodies.

A further alternative is to generate novel VH or VL regions carrying the CDR-derived sequences of the invention using random mutagenesis of, for example, the Ab VH or VL genes to generate mutations within the entire variable domain. Such a technique is described by Gram et al (1992, Proc. Natl. Acad. Sci., USA, 89:3576-3580), who used error-prone PCR. Another method which may be used is to direct mutagenesis to CDR regions of VH or VL genes. Such techniques are disclosed by Barbas et al, (1994, Proc. Natl. Acad. Sci., USA, 91:3809-3813) and Schier et al (1996, J. Mol. Biol. 263:551-567).

All the above described techniques are known as such in the art and in themselves do not form part of the present invention. The skilled person will be able to use such techniques to provide specific binding members of the invention using routine methodology in the art.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as provided herein and/or known to those of skill in the art.

Although in a preferred aspect of the invention specific binding members comprising a pair of binding domains based on sequences substantially set out in FIGS. 2 and/or 10 are preferred, single binding domains based on either of these sequences form further aspects of the invention. In the case of the binding domains based on the sequence substantially set out in FIGS. 2 and/or 10, such binding domains may be used as targeting agents for FAP on stromal cells, particularly tumor stroma, since it is known that immunoglobulin VH domains are capable of binding target antigens in a specific manner.

This may be achieved by phage display screening methods using the so-called hierarchical dual combinatorial approach as disclosed in U.S. Pat. No. 5,969,108 in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al, ibid. Phage library and phage display selection systems and techniques are also provided herein.

Specific binding members of the present invention may further comprise antibody constant regions or parts thereof. For example, specific binding members based on the sequences of FIGS. 2 and 10 may be attached at their C-terminal end to antibody light chain constant domains including human Cκ or Cλ chains, preferably Cλ chains. Similarly, specific binding members based on the sequences of FIG. 10, 12 or 13 may be attached at their C-terminal end to all or part of an immunoglobulin heavy chain derived from any antibody isotype, e.g. IgG, IgA, IgE, IgD and IgM and any of the isotype sub-classes, particularly IgG1, IgG2b, and IgG4. IgG1 is preferred.

The antibodies, or any fragments thereof, may be conjugated or recombinantly fused to any cellular toxin, bacterial or other, e.g. pseudomonas exotoxin, ricin, or diphtheria toxin. The part of the toxin used can be the whole toxin, or any particular domain of the toxin. Such antibody-toxin molecules have successfully been used for targeting and therapy of different kinds of cancers, see e.g. Pastan, Biochim Biophys Acta. 1997 Oct. 24; 1333(2):C1-6; Kreitman et al., N Engl J. Med. 2001 Jul. 26; 345(4):241-7; Schnell et al., Leukemia. 2000 January; 14(1):129-35; Ghetie et al., Mol. Biotechnol. 2001 July; 18(3):251-68.

Bi- and tri-specific multimers can be formed by association of different scFv molecules and have been designed as cross-linking reagents for T-cell recruitment into tumors (immunotherapy), viral retargeting (gene therapy) and as red blood cell agglutination reagents (immunodiagnostics), see e.g. Todorovska et al., J Immunol Methods. 2001 Feb. 1; 248(1-2):47-66; Tomlinson et al., Methods Enzymol. 2000; 326:461-79; McCall et al., J. Immunol. 2001 May 15; 166(10):6112-7.

Fully human antibodies can be prepared by immunizing transgenic mice carrying large portions of the human immunoglobulin heavy and light chains. These mice, examples of such mice are the Xenomouse™ (Abgenix, Inc.) (U.S. Pat. Nos. 6,075,181 and 6,150,584), the HuMAb-Mouse™ (Medarex, Inc./GenPharm) (U.S. Pat. Nos. 5,545,806 and 5,569,825), the TransChromo Mouse™ (Kirin) and the KM Mouse™ (Medarex/Kirin), are well known within the art. Antibodies can then be prepared by, e.g. standard hybridoma technique or by phage display. These antibodies will then contain only fully human amino acid sequences. Fully human antibodies can also be generated using phage display from human libraries. Phage display may be performed using methods well known to the skilled artisan, and as provided herein as in Hoogenboom et al and Marks et al (Hoogenboom H R and Winter G. (1992) J Mol. Biol. 227(2):381-8; Marks J D et al (1991) J Mol. Biol. 222(3):581-97; and also U.S. Pat. Nos. 5,885,793 and 5,969,108).

Antibodies of the invention may be labelled with a detectable or functional label. Detectable labels include, but are not limited to, radiolabels such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{121}I$, $^{124}I$, $^{125}I$, $^{131}I$, $^{111}In$, $^{117}Lu$, $^{211}At$, $^{198}Au$, $^{67}Cu$, $^{225}Ac$, $^{213}Bi$, $^{99}Tc$ and $^{186}Re$, which may be attached to antibodies of the invention using conventional chemistry known in the art of antibody imaging. Labels also include fluorescent labels (for example fluorescein, rhodamine, Texas Red) and labels used conventionally in the art for MRI-CT imaging. They also include enzyme labels such as horseradish peroxidase, β-glucoronidase, β-galactosidase, urease. Labels further include chemical moieties such as biotin which may be detected via binding to a specific cognate detectable moiety, e.g. labelled avidin. Functional labels include substances which are designed to be targeted to the site of a tumor to cause destruction of tumor tissue. Such functional labels include cytotoxic drugs such as 5-fluorouracil or ricin and enzymes such as bacterial carboxypeptidase or nitroreductase, which are capable of converting prodrugs into active drugs at the site of a tumor.

Also, antibodies including fragments thereof, and drugs that modulate the production or activity of the specific binding members, antibodies and/or their subunits may possess certain diagnostic applications and may for example, be utilized for the purpose of detecting and/or measuring conditions such as cancer, precancerous lesions, conditions related to or resulting from hyperproliferative cell growth or the like. For example, the specific binding members, antibodies or their subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the specific binding members of the invention may be discovered or synthesized, and may be used in diagnostic and/or therapeutic protocols.

The radiolabelled specific binding members, particularly antibodies and fragments thereof, are useful in in vitro diagnostics techniques and in in vivo radioimaging techniques and in radioimmunotherapy. In the instance of in vivo imaging, the specific binding members of the present invention may be conjugated to an imaging agent rather than a radioisotope(s), including but not limited to a magnetic resonance image enhancing agent, wherein for instance an antibody molecule is loaded with a large number of paramagnetic ions through chelating groups. Examples of chelating groups include EDTA, porphyrins, polyamines crown ethers and polyoximes. Examples of paramagnetic ions include gadolinium, iron, manganese, rhenium, europium, lanthanum, holmium and ferbium. In a further aspect of the invention, radiolabelled specific binding members, particularly antibodies and fragments thereof, particularly radioimmunoconjugates, are useful in radioimmunotherapy, particularly as radiolabelled antibodies for cancer therapy. In a still further aspect, the radiolabelled specific binding members, particularly antibodies and fragments thereof, are useful in radioimmuno-guided surgery techniques, wherein they can identify and indicate the presence and/or location of cancer cells, precancerous cells, tumor cells, and hyperproliferative cells, prior to, during or following surgery to remove such cells.

Immunoconjugates or antibody fusion proteins of the present invention, wherein the specific binding members, particularly antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

Radioimmunotherapy (RAIT) has entered the clinic and demonstrated efficacy using various antibody immunoconjugates. $^{131}$I labeled humanized anti-carcinoembryonic antigen (anti-CEA) antibody hMN-14 has been evaluated in colorectal cancer (Behr T M et al (2002) Cancer 94(4Suppl):1373-81) and the same antibody with $^{90}$Y label has been assessed in medullary thyroid carcinoma (Stein R et al (2002) Cancer 94(1):51-61). Radioimmunotherapy using monoclonal antibodies has also been assessed and reported for non-Hodgkin's lymphoma and pancreatic cancer (Goldenberg DM (2001) Crit Rev Oncol Hematol 39(1-2):195-201; Gold D V et al (2001) Crit Rev Oncol Hematol 39 (1-2) 147-54). Radioimmunotherapy methods with particular antibodies are also described in U.S. Pat. Nos. 6,306,393 and 6,331,175. Radioimmunoguided surgery (RIGS) has also entered the clinic and demonstrated efficacy and usefulness, including using anti-CEA antibodies and antibodies directed against tumor-associated antigens (Kim J C et al (2002) Int J Cancer 97(4):542-7; Schneebaum S et al (2001) World J Surg 25(12): 1495-8; Avital S et al (2000) Cancer 89(8):1692-8; McIntosh D G et al (1997) Cancer Biother Radiopharm 12 (4):287-94).

In vivo animal models of cancer or animal xenograft studies may be utilized by the skilled artisan to further or additionally screen, assess, and/or verify the specific binding members and antibodies or fragments thereof of the present invention, including further assessing FAP modulation and inhibiting stromal cell adhesion to ECM proteins in vivo and inhibiting tumor progression and/or infiltration. Such animal models include, but are not limited to models of conditions associated with activated stroma, including wound healing, epithelial cancers, osteoarthritis, rheumatoid arthritis, cirrhosis and pulmonary fibrosis, particularly without the problems associated with normal tissue uptake. Models of cancers whose progression, migration and/or invasion involves, is facilitated by, or is associated with stromal fibroblasts are particularly susceptible to and targeted by the antibodies of the present invention. Such cancers include epithelial cancers, including breast, lung, colorectal and ovarian cancer. For example but without limitation, the mouse sarcoma cell line 1 m8 expresses high levels of FAP and grows in syngeneic C3h mice. This may be utilized in xenograft experiments or in a sarcoma model for direct tumor targeting and/or to assess anti-tumor and anti-cancer effects of the anti-FAP antibodies.

Antibodies of the present invention may be administered to a patient in need of treatment via any suitable route, including by injection intramuscularly, into the bloodstream or CSF, or directly into the site of the tumor. The precise dose will depend upon a number of factors, including whether the antibody is for diagnosis or for treatment, the size and location of the tumor, the precise nature of the antibody (whether whole antibody, fragment, diabody, etc), and the nature of the detectable or functional label attached to the antibody. Where a radionuclide is used for therapy, a suitable maximum single dose may be about 45 mCi/m$^2$, to a maximum of about 250 mCi/m$^2$. Preferable dosage is in the range of 15 to 40 mCi, with a further preferred dosage range of 20 to 30 mCi, or 10 to 30 mCi. Such therapy may require bone marrow or stem cell replacement. A typical antibody dose for either tumor imaging or tumor treatment will be in the range of from 0.5 to 40 mg, preferably from 1 to 4 mg of antibody in F(ab')2 form. Naked antibodies are preferably administered in doses of 20 to 1000 mg protein per dose, or 20 to 500 mg protein per dose, or 20 to 100 mg protein per dose. This is a dose for a single treatment of an adult patient, which may be proportionally adjusted for children and infants, and also adjusted for other antibody formats, in proportion for example to molecular weight. Treatments may be repeated at daily, twice-weekly, weekly or monthly intervals, at the discretion of the physician.

Pharmaceutical and Therapeutic Compositions

Specific binding members of the present invention will usually be administered in the form of a pharmaceutical composition, which may comprise at least one component in addition to the specific binding member. Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous, or by deposition at a tumor site.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient may be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, therapeutics or agents, either simultaneously or sequentially dependent upon the condition to be treated. In addition, the present invention contemplates and includes compositions comprising the binding member, particularly antibody or fragment thereof, herein described and other agents or therapeutics such as anti-cancer agents or therapeutics, hormones, anti-mitotic agents, anti-apoptotic agents, antibodies, or immune modulators. More generally these anti-cancer agents may be but are not limited to tyrosine kinase inhibitors or phosphorylation cascade inhibitors, post-translational modulators, cell growth or division inhibitors (e.g. anti-mitotics), or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. The composition can be administered in combination (either sequentially (i.e. before or after) or simultaneously) with tyrosine kinase inhibitors (including, but not limited to AG1478 and ZD1839, STI571, OSI-774, SU-6668), doxorubicin, temozolomide, cisplatin, carboplatin, nitrosoureas, procarbazine, vincristine, hydroxyurea, 5-fluoruracil, cytosine arabinoside, cyclophosphamide, epipodophyllotoxin, carmustine, lomustine, and/or other chemotherapeutic agents. Thus, these agents may be specific anti-cancer agents, or immune cell response modulators or may be more general anti-cancer and anti-neoplastic agents such as doxorubicin, cisplatin, temozolomide, nitrosoureas, procarbazine, vincristine, hydroxyurea, 5-fluoruracil, cytosine arabinoside, cyclophosphamide, epipodophyllotoxin, carmustine, or lomustine. In addition, the composition may be administered with hormones such as dexamethasone, immune modulators, such as interleukins, tumor necrosis factor (TNF) or other growth factors, colony stimulating factors, or cytokines which stimulate the immune response and reduction or elimination of cancer cells or tumors. The composition may also be administered with, or may include combinations along with other anti-tumor antigen antibodies.

In addition, the present invention contemplates and includes therapeutic compositions for the use of the binding member in combination with conventional radiotherapy.

The present invention further contemplates therapeutic compositions useful in practicing the therapeutic methods of this invention. A subject therapeutic composition includes, in admixture, a pharmaceutically acceptable excipient (carrier) and one or more of a specific binding member, polypeptide analog thereof or fragment thereof, as described herein as an active ingredient. In a preferred embodiment, the composition comprises an antigen capable of modulating the specific binding of the present binding member/antibody with a target cell.

The preparation of therapeutic compositions which contain polypeptides, analogs or active fragments as active ingredients is well understood in the art. Typically, such compositions are prepared as injectables, either as liquid solutions or suspensions. However, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic antibody- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of peptide/MHC or tumor antigen binding capacity desired. Precise amounts of active ingredient required to be administered depend on the judgment of the practitioner and are peculiar to each individual. Suitable regimes for initial administration and follow on administration are also variable, and may include an initial administration followed by repeated doses at one or more hour intervals by a subsequent injection or other administration. Alternatively, continuous intravenous infusion sufficient to maintain appropriate and sufficient concentrations in the blood or at the site of desired therapy are contemplated.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Diagnostic Assays

The present invention also relates to a variety of diagnostic applications, including methods for detecting the expression of or elevated presence of FAP, FAP-mediated mediated cancer, epithelial cancer, or cancer more generally, wound healing, osteoarthritis, by reference to their ability to be recognized by the present specific binding member(s). Peptide complexes can be identified, targeted, labeled, and/or quantitated on stromal cells, fibroblast cells and/or tumor cells.

Diagnostic applications of the specific binding members of the present invention, particularly antibodies and fragments thereof, include in vitro and in vivo applications well known and standard to the skilled artisan and based on the present description. Diagnostic assays and kits for in vitro assessment and evaluation of tumor and cancer status, may be utilized to diagnose, evaluate and monitor patient samples including those known to have or suspected of having cancer, a precancerous condition, a condition related to hyperproliferative cell growth or from a tumor sample. The assessment and evaluation of cancer, tumor and metastatic disease status is also useful in determining the suitability of a patient for a clinical trial of a drug or for the administration of a particular chemotherapeutic agent or specific binding member, particularly an antibody, of the present invention, including combinations thereof, versus a different agent or binding member. This type of diagnostic monitoring and assessment is already in practice utilizing antibodies against the HER2 protein in breast cancer (Hercep Test, Dako Corporation), where the assay is also used to evaluate patients for antibody therapy using Herceptin. In vivo applications include imaging of tumors or assessing cancer status of individuals, including radioimaging.

Preferably, the antibody used in the diagnostic methods of this invention is human antibody. More preferably, the antibody is a single chain chain antibody or domain antibody. In addition, the antibody molecules used herein can be in the form of Fab, Fab', F(ab')$_2$ or F(v) portions of whole antibody molecules, particularly Fab.

As described in detail above, antibody(ies) to FAP can be produced and isolated by standard methods including the phage display techniques and mutagenesis and recombinant techniques.

The presence of FAP in cells can be ascertained by the usual in vitro or in vivo immunological procedures applicable to such determinations. A number of useful procedures are known. The procedures and their application are all familiar to those skilled in the art and accordingly may be utilized within the scope of the present invention. The "competitive" procedure is described in U.S. Pat. Nos. 3,654,090 and 3,850,752. The "sandwich" procedure, is described in U.S. Pat. Nos. RE 31,006 and 4,016,043. Still other procedures are known such as the "double antibody," or "DASP" procedure.

In a further embodiment of this invention, commercial test kits suitable for use by a medical specialist may be prepared to determine the presence or absence of aberrant expression of including but not limited to amplified and/or an mutation, in suspected target cells. In accordance with the testing techniques discussed above, one class of such kits will contain at least the labeled or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence of or elevated levels of FAP, comprising:

(a) a predetermined amount of at least one labeled immunochemically reactive component obtained by the direct or indirect attachment of the present specific binding member or a specific binding partner thereto, to a detectable label;

(b) other reagents; and (c) directions for use of said kit.

A test kit may be prepared for the demonstration of the presence of epithelial cancer, stromal cell mediated cancer, particularly selected from breast, lung, colorectal, ovarian cancer comprising:

(a) a predetermined amount of at least one labeled immunochemically reactive component obtained by the direct or indirect attachment of the present specific binding member or a specific binding partner thereto, to a detectable label;

(b) other reagents; and (c) directions for use of said kit.

In accordance with the above, an assay system for screening potential drugs effective to modulate the presence or activity of FAP and/or the activity or binding of the antibody of the present invention may be prepared. The antigen peptide or the binding member or antibody may be introduced into a test system, and the prospective drug may also be introduced into the resulting cell culture, and the culture thereafter examined to observe any changes in the activity of the cells, binding of the antibody, or amount and extent of FAP due either to the addition of the prospective drug alone, or due to the effect of added quantities of the known agent(s).

Nucleic Acids

The present invention further provides an isolated nucleic acid encoding a specific binding member of the present invention. Nucleic acid includes DNA and RNA. In a preferred aspect, the present invention provides a nucleic acid which codes for a polypeptide of the invention as defined above, including a polypeptide as set out in FIG. 2 or 10 or capable of encoding the CDR regions thereof.

The present invention also provides constructs in the form of plasmids, vectors, transcription or expression cassettes which comprise at least one polynucleotide as above. The present invention also provides a recombinant host cell which comprises one or more constructs as above. A nucleic acid encoding any specific binding member as provided itself forms an aspect of the present invention, as does a method of production of the specific binding member which method comprises expression from encoding nucleic acid therefor. Expression may conveniently be achieved by culturing under appropriate conditions recombinant host cells containing the nucleic acid. Following production by expression a specific binding member may be isolated and/or purified using any suitable technique, then used as appropriate.

Specific binding members and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, cancer cells, ovarian cancer cells and many others. A common, preferred bacterial host is *E. coli*. The expression of antibodies and antibody fragments in prokaryotic cells such as *E. coli* is well established in the art.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. The present invention also provides a method which comprises using a construct as stated above in an expression system in order to express a specific binding member or polypeptide as above.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host. A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col El, pCR1, pBR322, pMB9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors a person skilled in the art will be able to construct a variety of vector/expression control sequence/host combinations that will express the DNA sequences of this invention on fermentation or in large scale animal culture.

As mentioned above, a DNA sequence encoding a specific binding member can be prepared synthetically rather than cloned. The DNA sequence can be designed with the appropriate codons for the specific binding member amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984). Synthetic DNA sequences allow convenient construction of genes which will express specific binding member analogs or "muteins". Alternatively, DNA encoding muteins can be made by site-directed mutagenesis of native specific binding member genes or cDNAs, and muteins can be made directly using conventional polypeptide synthesis.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

Fibroblast Activation Protein (FAP) is a member of the dipeptidyl peptidase IV (DPPIV, CD26) protein family and capable of cleaving N-terminal dipeptides from polypeptides with proline or alanine in the penultimate position. FAP expression is up-regulated on activated fibroblasts such as carcinoma-associated fibroblasts and promotes malignant and invasive behaviour. We selected fully human Fab antibodies from a phage library that are cross-reactive to mouse and human FAP. The most frequently identified clones, ESC11 and ESC14, were chosen for further analysis since no binding to the highly homologous CD26 antigen was detected. Both antibodies are binding to FAP at low nanomolar affinities when converted into human IgG antibodies and could be produced in mammalian cell lines at high levels. ESC11 and ESC14 antibodies had no direct influence on the dipeptidyl peptidase IV activity of FAP induced conversion of a FAP-positive into a FAP-negative phenotype was paralleled by a significantly inhibited adhesion of targeted cells to ECM proteins and enhanced target cell apoptosis. With respect to the disease restricted expression pattern of FAP, our data strongly provide evidence for a clinical development plan of ESC11 and ESC14 in areas where fibroblast dependent malignant and invasive behaviour is of relevance.

INTRODUCTION

Fibroblast activation protein (FAP) was originally identified as a serine protease on reactive stromal fibroblasts [1, 2]. Subsequent molecular cloning revealed that FAP is identical to seprase, a 170 kDa membrane associated gelatinase that is expressed by melanoma cell lines [3, 4]. Full length cDNA encoded a type II transmembrane protease of 760 amino acids (aa) highly homologous to dipeptidyl peptidase IV (DPPIV) with a 52% aa identity over the entire sequence and almost 70% identity in the catalytic domain [3, 5]. FAP and DPPIV have similar gene sizes and are chromosomally adjacent to each other at 2q24, suggesting a gene duplication event (Genebank accession number U09278). Both proteins are members of the prolyl peptidase family [1, 6]. This class of enzymes is inducible, active on the cell surface or in extracellular fluids, and uniquely capable of cleaving N-terminal dipeptides from polypeptides with proline or alanine in the penultimate position [7]. DPPIV, also termed CD26, is constitutively expressed by several cell types including fibroblasts, endothelial and epithelial cells, leukocyte subsets like NK-cells, T-lymphocytes and macrophages. A small proportion of DPPIV circulates as soluble protein in the blood. In contrast to DPPIV, FAP is typically not expressed in normal adult tissue [1] and its proteolytically active soluble form is termed a2-Antiplasmin Cleaving Enzyme (APCE) [8]. Marked FAP expression occurs in conditions associated with activated stroma, including wound healing, epithelial cancers, osteoarthritis, rheumatoid arthritis, cirrhosis and pulmonary fibrosis [4, 9-11].

The FAP structure has been solved (PDB ID 1Z68) and is very similar to that of DPPIV [12]. FAP is anchored in the plasma membrane by an uncleaved signal sequence of approximately 20 aa and has a short, amino terminal, cytoplasmic domain of six aa [3-5]. The major part of the protein, including the catalytic domain, is exposed to the extracellular environment [13]. The FAP glycoprotein is a homodimer consisting of two identical 97-kDa subunits. Each FAP-monomer subunit consists of two domains, an αβ hydrolase domain (aa 27-53 and 493-760) and an eight-blade β propeller domain (aa 54-492) that enclose a large cavity. A small pocket within this cavity at the interface of both domains contains the catalytic triad (Ser624, Asp702 and His734) [12]. FAP gains its enzymatic activity upon homodimerization of the subunits [14] and beside its dipeptidyl peptidase activity, FAP also has collagen type I specific gelatinase [15] and endopeptidase activity [16]. The β propeller acts as scaffolding for protein-protein interactions and determines substrate and extracellular matrix (ECM) binding [17]. Furthermore, the β propeller is involved in forming supra-molecular complexes of FAP with other prolyl peptidases or with other membrane-bound molecules [18, 19]. The formation of heteromeric or tetrameric complexes of FAP and DPPIV were found to be associated with invadopodia of migrating cells on a collagen substrate [20]. Type I collagen induces a close association of FAP with β1 integrins, thereby playing major organizational roles in the formation and adhesion of invadopodia [21]. Although the involved mechanisms are not understood in detail, the formation of such proteinase-rich membrane domains at the cellular invasion front contributes to directed pericellular ECM degradation [22]. This indicates that FAP and ECM interactions may be closely related to invasive cell behaviour by influencing cell adhesion, migration, proliferation and apoptosis through integrin pathways [19, 21, 23] and supports o role of FAP in disease pathogenesis and progression [24]. In summary, FAP is recognized as a multifunctional protein that executes its biological functions in a cell dependent manner through a combination of its protease activity and its ability to form complexes with other cell-surface molecules. Over-expression of FAP in epithelial and fibroblastic cell lines promotes malignant behaviour [22], pointing to the clinical situation, where cellular expression levels of FAP are correlated with worse clinical outcome [25, 26].

The morphological and functional properties promote the investigation of FAP as a therapeutic target. The disease related and cell surface bound expression pattern especially qualifies FAP for antibody targeting. With regard to the pathophysiological involvement in ECM remodelling, targeting strategies should aim at the disruption of the signalling supramolecular FAP complexes. Here, we describe the generation of novel anti-FAP antibodies with cross reactivity for murine and human FAP, providing applicability in biologically relevant test systems. Additional pre-absorption steps on DPPIV/CD26 immunoprecipitate suspension during the selection process removed unwanted antibodies, cross-reactive with this ubiquitously expressed FAP-homologue. The challenge of targeted disruption of protein-protein interactions was accepted, since incubation with novel anti-FAP antibodies significantly inhibited adhesion of targeted cells to ECM proteins and induced apoptotic signals.

Materials and Methods

Recombinant Expression of Antigens.

Human FAP and DPPIV/CD26 cDNA was obtained from pooled nasopharynx carcinoma and spleen tissue, respectively. Murine FAP cDNA was obtained from lung and skin tissue. The antigens were cloned into pEAK 8 vector (Edge Biosystems) and stably expressed in HEK293 c-18 cells (ATCC CRL-10852) using the FuGene6 transfection reagent (Roche) according to the manufacturers instructions. The stable cell lines were grown in DMEM supplemented with 10% FBS, penicillin-streptomycin, and puromycin (3 μg/ml). Monoclonal cultures were obtained by limited dilution.

Immunoprecipitation of Recombinant FAP.

$5 \times 10^7$ HEK293 cells expressing human FAP or mock-transfected cells were solubilized in 5 ml lysis buffer (50 mM Tris-HCl, 150 mM NaCl buffer, pH 7.4, 0.7% w/v β-octyl-glucopyranoside) by vortexing for 15 min at 4° C. Cell debris was removed by centrifugation and the supernatant was incubated for 4 hr at 4° C. with 50 μl protein A magnetic beads (Dynabeads, invitrogen) coated with monoclonal antibody F19. Beads were removed from suspension using a magnetic rack and washed five times with PBS 0.1% Tween 20 and stored at −80° C. in 100 μl PBS. Accordingly, recombinant DPPIV/CD26 was immunoprecipitated with an anti-CD26 mAb. Immunoprecipitates were subjected to SDS-PAGE, western blot analysis and dipeptidyl-peptidase activity assay.

Selection of Antibodies by Phage Display.

For selection of huFAP-muFAP specific antibodies, a non-immunized phage library expressing antibody Fab fragments was used [27]. $10^{13}$ Phages were blocked in 2% milk powder in PBS and preabsorbed with 25 μl of immunoprecipitate prepared from the mock-transfected cell line to remove phages that bind to protein A beads and F19 mAb. Preabsorbed phages were incubated with huFAP containing immunoprecipitates for 1 h at RT, washed with PBS 0.1% Tween 20 and with PBS, and subsequently eluted with 100 mM triethylamine. Neutralized phages were amplified in *Escherichia coli* TG-1 using M13K07 as helper phage. Four rounds of selection with decreasing antigen concentration were performed (50, 25, 12.5, and 6.5 μl of immunoprecipitate suspension). To enrich the phage pool for binders that recognize muFAP, a fifth round was appended by incubating the phages with HEK293 muFAP expressing cells. Prior to selection rounds four and five, an additional preabsorption step on 50 μl DPPIV/CD26 immunoprecipitate suspension was included to remove FAP-binders that cross-react with DPPIV/CD26.

Screening of Supernatants by ELISA and Flow Cytometry.

Supernatants of the output libraries after each selection round, and supernatants of individual bacterial clones after rounds three, four and five were screened for FAP-binding phage by ELISA. Ninety-six-well microtiter plates (MAXI-SORP® Nunc) were coated with cell extracts cell extracts from HEK293 huFAP, HEK293 huCD26, HEK293 muFAP, or mock-transfected HEK293, blocked with 5% milk powder in PBS, incubated with phage-containing supernatants for 1 hr at room temperature and developed using an anti-M13-HRP conjugated antibody. Positive clones were induced with 1 mM IPTG to produce soluble Fab and further screened for binding specificities using flow cytometry on antigen expressing HEK293 cell lines. Bound Fab antibody was detected with anti-myc tag antibody 9E10, followed by an anti-mouse immunoglobulin-PE conjugate. For competition assays, Fab antibodies were detected using biotinylated anti-myc tag 9E10, followed by strep-PE.

Expression of Fab Fragments.

Fab fragments were produced in *E. coli* TG-1 by induction with 1 mM IPTG for 4 hr at 30° C. Soluble Fab was released from the periplasmic fraction by incubation in PBS, pH 8 at 4° C. o/n, purified using His-tag purification with TALON® TALON beads and analyzed by SDS-PAGE.

Determination of Kinetic Rate Constants and Affinity by Surface Plasmon Resonance.

Binding analysis of Fabs to recombinant FAP (R&D systems) was performed on a BIAcore T100 instrument. rFAP was immobilized at low density on a CM5 sensor chip using amine coupling chemistry. For analysis of the kinetics, various concentrations (range 0.5-16 nM for ESC11 and 6.25-200 nM for ESC14) of Fabs in flow buffer (HBS-EP: 10 mM HEPES, pH 7.4, containing 3.4 mM EDTA, 0.15 mM NaCl, and 0.005% Tween 20) were injected at a flow rate of 50 μl/min at 25° C. Analysis of the binding curves and determination of rate constants was done using the nonlinear data analysis program BIAevaluation.

Determination of the Apparent KD (Kd(app)).

To determine the Kd(app), $2.5 \times 10^5$ human or mouse FAP expressing HT1080hFAP and 293mFAP, respectively, were incubated with serial dilutions of the indicated constructs for 20 min at 4° C. The cells were then washed once with PBS, fixed for 20 min with 2% PFA on ice and bound antibody was detected with PE-conjugated anti-human IgG F(ab)'$_2$ (Jackson Immuno Research 109-116-097). Cells were analyzed on a FACSCAN® (BD) cytometer and data was analysed with FlowJo. The apparent Kapp was calculated by fitting a dose-response curve using the following equitation f=Bmax*abs(x)/(Kd+abs(x))+Ns*x using SIGMAPLOT® software (Systat Software Inc.).

Fluorogenic Dipeptidyl Peptidase Activity Assay.

For enrichment of membrane proteins, $10^7$ HEK293 cells expressing antigen were resuspended in 50 mM Tris-HCl, 150 mM NaCl buffer, pH 7.4, 2% w/v Triton-X114 and incubated for 15 min on ice. Cellular debris was removed by centrifugation at 14000 rpm for 5 min at 4° C. The supernatant was warmed to 30° C. for 10 mM and phase separatiori was performed by centrifugation at RT. The detergent phase was washed with 1 ml AFC-reaction buffer (100 mM NaCl, 100 mM Tris, pH 7.8), phase-partitioned, and diluted 1:10 in AFC reaction buffer. The diluted extracts were incubated with 0.5 mM Ala-Pro-AFC in 96-well plates at 37° C. and release of free AFC was monitored over time on a fluorescence reader (Victor Wallac, Perkin Elmer), using a 395 nm excitation/530 nm emission filter set. Dipeptidyl peptidase activity was determined from the slope of the fluorescence readings, after subtraction of background activity from a FAP negative sample. Dipeptidyl peptidase activity was inhibited using PT-100 (Sigma). PT-100 inhibits dipeptidyl peptidases and structural homologues. PT-100 was incubated at indicated concentrations with membrane extracts for 15 min prior to the addition of Ala-Pro-AFC substrate as described [28] and inhibition of dipeptidyl peptidase activity was measured as described above.

Cloning, Expression, and Purification of IgG1.

The variable sequences of heavy and light chain were cloned into a modified pEE12.4 vector (Lonza biologics) expressing human constant IgG1 regions via DraIII and RsrII sites, respectively, with a PCR cloning kit (IN-FUSION®, Clontech). The plasmid was linearized with PvuI, and transfected into GS-NSO cells (Lonza biologics) by electroporation. Positive clones were selected in glutamine-free medium with methionine sulphoximine. Stable cell lines were grown in glutamine-free medium with 5% FCS, which has been depleted from bovine IgG with protein G sepharose. IgG was purified from culture supernatant with protein A sepharose.

FAP staining of Fibroblasts.

$10^5$ human fibroblasts were incubated with 10 ug/ml of the indicated antibodies for 20 min at 4° C. Bound antibody was detected with PE-conjugated anti-human IgG F(ab)'$_2$ (Jackson immune Research 109-116-097) for the ESC 11IgG, ESC14IgG and the human FAP specific control antibody. The parental murine F19 was detected with a FITC conjugated anti-human IgG (BD Pharmingen 555988). Cells were analyzed on a FACSCAN® (BD) cytometer and data analysed with FlowJo.

Antibody Mediated Down-Regulation of FAP Expression.

For detection of loss of FAP expression, sub-confluent HT1080FAP cultures were trypsinized, washed with PBS and resuspended in RPMI, 10% FBS at $5 \times 10^5$ cells and 0.5 ml per well seeded in 12 well cell culture plates and the indicated concentration of ESCHIgG was added. After over night incubation, cells were trypsinized washed and stained with 10 ug/ml F19 followed by FITC-conjugated polyclonal goat anti-mouse. Fluorescence intensity of the cells was analyzed by flow cytometry. % FAP expression was calculated (100/(signal 0 ug/ml ESC11IgG−background signal))*(signal with ESC11IgG−backgroundsignal). One representative of three independent experiments is shown.

Competition Assay.

For measuring the competitive binding of ESC11 and ESC14, Fab fragments were titered on HT1080hFAP cells and binding was determined by flow cytometry. The concentration resulting in 90% of the maximal binding was used for the competition assay. HT1080FAP were incubated with the indicated antibodies at 5 ug/ml for 20 min at 4° C., then the ESC11-/ESC14 Fab fragments or PBS added at the pre-determined concentrations and incubated for 20 min at 4° C. Cells were washed once with PBS at 4° C. and fixed with 2% PFA on ice. Bound Fab fragment was detected by the myc-tag with biotinylated anti-myc and PE conjugated streptavidin. Cells were then analyzed by flow cytometry as described.

Attachment Assay.

Ninety-six-well microtiter plates (MAXISORP®, Nunc) were coated with indicated proteins at a concentration of 50 ug/ml and incubated over night at 4° C. Plates were washed three times with PBS and then blocked with 1% BSA for 60 min at 37° C. Cells were preincubated for 30 min with indicated antibodies at a final concentration of 10 ug/ml and then added to the coated plates. After 60 min, plates were washed with PBS to remove non adherent cells. Attached cells were stained using cristal violet and lysed by addition of Isopropanol with 0.4M HCl at a final volume of 75 ul/well. OD560 was measured on a ELISA reader.

Detection of Apoptotic Cells by Annexin V Staining.

FAP- and mock-transfected Hek293 cells were incubated in DMEM supplemented with 10% FBS in the presence of indicated amount of antibodies at RT. Control samples were either incubated in the absence of antibodies or at 4° C. in the presence of antibodies. After 60 min, cells were washed and stained with Propidium Iodide (Sigma) and Annexin V (Roche) following the manufacturer's instructions and the percentage of apoptosis was determined using flow cytometry.

Results

Figure 3:
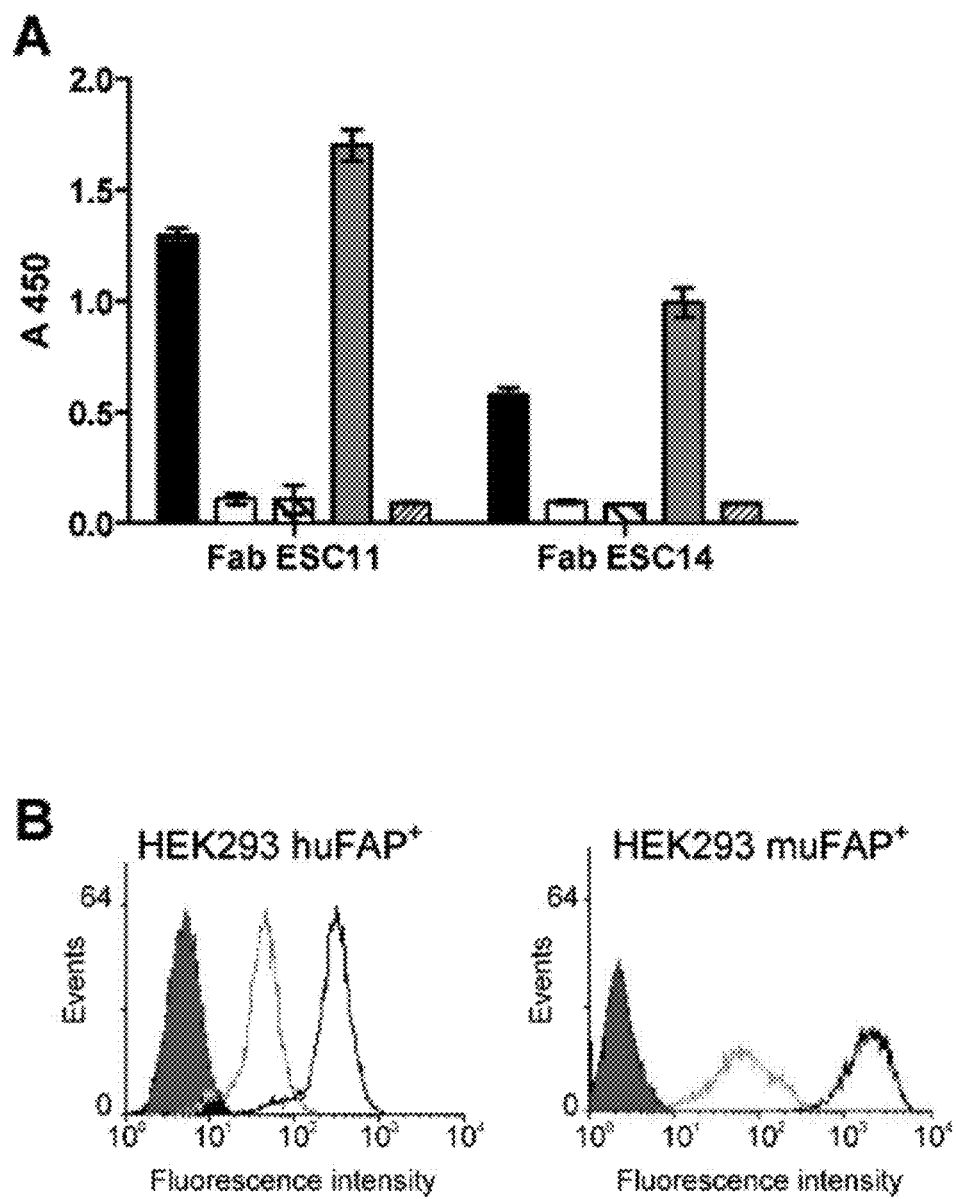
FIG. 3: Specificity of Fabs ESC11 and ESC14. A. ELISA of Fabs (100 nM) binding to cell-lysate-coated plates. HT1080 FAP$^+$ (black bars), HT1080 (white bars), HEK293 huCD26$^+$ (striped bars), HEK293 muFAP$^+$ (grey bars), HEK293 mock transfected line (hatched bars). B. FACS analysis of Fab ESC11 (black line), ESC14 (grey line), and a non-binding control Fab (filled) on HT1080 FAP$^+$ cells (left) and 293 muFAP$^+$ cells (right)
Figure 4:
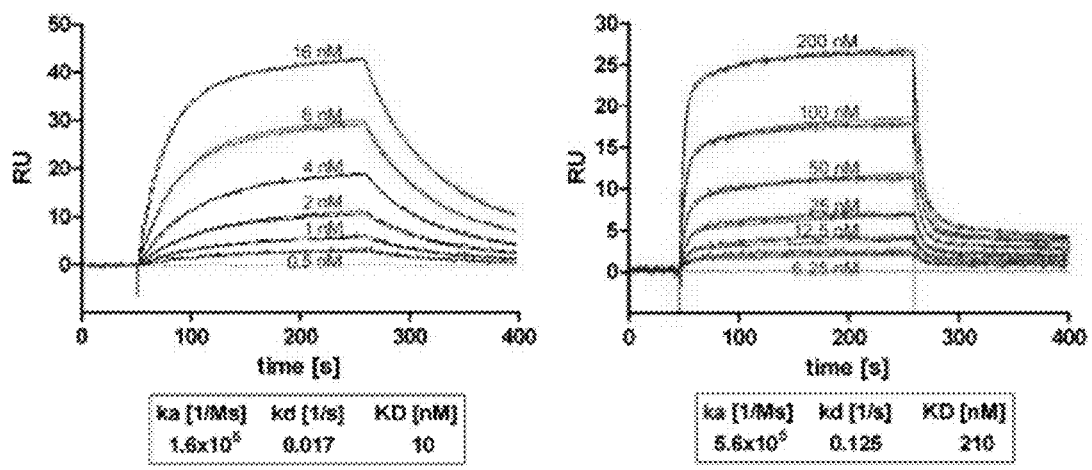
FIG. 4: Affinity of Fabs ESC11 and ESC14. Binding of Fabs ESC11 (left) and ESC14 (right) as monitored by surface plasmon resonance. Purified Fabs were injected at the concentrations indicated in the figure on a rhuFAP-coated CM5 sensor chip. Values were corrected for binding to the reference flow cell. The black solid lines represent the theoretical curves for each Fab concentration calculated according to the heterogeneous ligand model and the indicated rate and affinity constants.

Selection and Characterization of Mouse-Human FAP Cross-Reactive Antibody Fab Fragments Monoclonal antibody Fab-fragments were selected from a large human Fab antibody library by phage display on recombinant human FAP obtained by immunoprecipitation from stably transfected cell lysates. Briefly, lysates of HT1080 and FAP-transfected HT1080 (10) cells were separately incubated with magnetic protein A beads coated with a formerly described anti-huFAP antibody (11). FAP was immunoprecipitated from HT1080 FAP extracts at high purity (FIGS. 1A and B) and exhibited dipeptidyl-peptidase (DPP) activity (e.g. cleave the substrate Ala-Pro-AFC) when captured on magnetic beads (FIG. 1C). Unspecifically immunoprecipitated proteins binding to anti-huFAP antibody loaded magnetic beads after incubation with HT1080 cells ('mock-immunocapture') were used in pre-absorption steps. After four selection rounds, 5% of the phages bound to human FAP and 1% recognized both human and murine FAP (FIG. 1D). To further enrich for human-mouse cross-reactive binders, phages were panned on mouse FAP transfected HEK 293 cells for one additional selection round. Finally, 14% of the output phages bound to huFAP including 9% mouse-human cross-reactive phages. Subsequent screening of 300 clones by ELISA and sequencing of FAP-specific binders led to the identification of Fabs ESC 11 and ESC14 (FIG. 2). Both Fab fragments bound to human and murine FAP in a specific manner and did not cross-react with CD26 as pre-defined by our selection strategy (FIGS. 3A and B). Affinity measurements by surface plasmon resonance were performed on a low-density huFAP coated chip. $K_D$ values of 10±5 and 210±35 nM were determined for Fabs ESC 11 and ESC14, respectively (FIG. 4, Table 1). Affinities on muFAP were 51±11 nM for ESC 11 and 251±42 nM for ESC 14, as determined by serial dilutions on 293 muFAP+ cells (Table 1 Table 2).

TABLE 1

Affinities of anti-FAP antibodies on human and murine FAP

| | $K_D$ on huFAP [nM] | $K_D$ on muFAP [nM] |
|---|---|---|
| ESC11 Fab fragment | 10 ± 5 | 51 ± 11 |
| ESC14 Fab fragment | 210 ± 35 | 251 ± 42 |
| ESC11 IgG1 | 1.1 ± 0.1 | n.d. |
| ESC14 IgG1 | 1.1 ± 0.4 | n.d. |
| Anti-huFAP IgG1 | 4.2 ± 0.6 | n.d. |

Production and Characterization of IgG1 Antibodies ESC11 and ESC14

Figure 5:
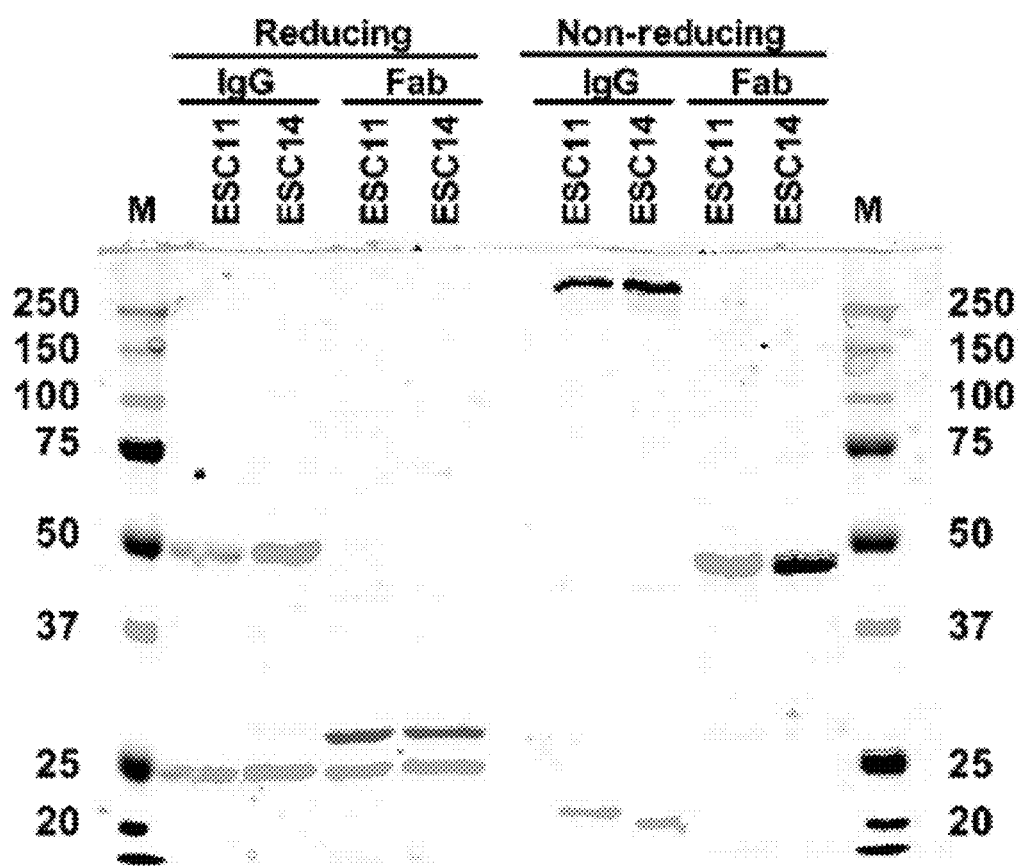
FIG. 5: Coomassie blue stained SDS-PAGE gel of 5 μg ESC11 and ESC14 IgGs and antibody Fab fragments under reducing and non-reducing conditions.
Figure 6:
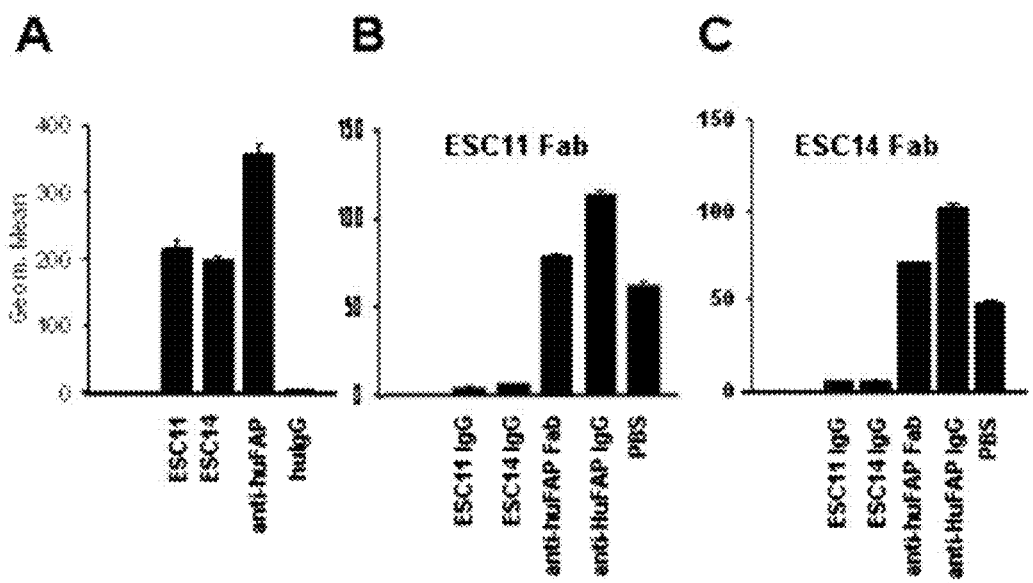
FIGS. 6A and B: FACS analysis of competitive FAP-binding relative to DPP activity. A. Binding of purified IgG to cultured FAP-expressing human fibroblasts. B. Cultured fibroblasts were incubated with ESC11 IgG or C. ESC14 IgG prior to the addition of competing Fab antibodies.

The variable heavy (HC) and light (LC) chain domains of ESC 11 and ESC14 were cloned into a full human IgG1 format. The original sequence obtained for the ESC11 HC could not been expressed in mammalian cells because of an anusual Histidine (H) in position 1 of the mature HC amino-acid sequence. The problem was solved when the Histidine was replaced by Glutamine (Q) (FIG. 2). IgGs were produced in NSO cells and purified by affinity chromatography on Protein A agarose from cell culture supernatant (FIG. 5). Binding of purified IgG to FAP was confirmed by flow cytometry using FAP-transfected HT1080 cells (FIG. 6A). Affinities on antigen expressing cell lines were higher for the bivalent IgGs with apparent $K_D$ values around 1 nM on human FAP (Table 1 Table 2). Competition assay demonstrated cross-inhibition for ESC 11 IgG (FIG. 6B) and ESC14 IgG (FIG. 6C), while anti-huFAP antibody did not compete for FAP binding. These results suggest that antibodies ESC11 and ESC14 recognise overlapping or closely linked epitopes that are clearly distinct from the epitope recognised by anti-hu FAP antibody.

Reactivity of Anti-FAP Antibodies to Activated Fibroblasts

Figure 7:
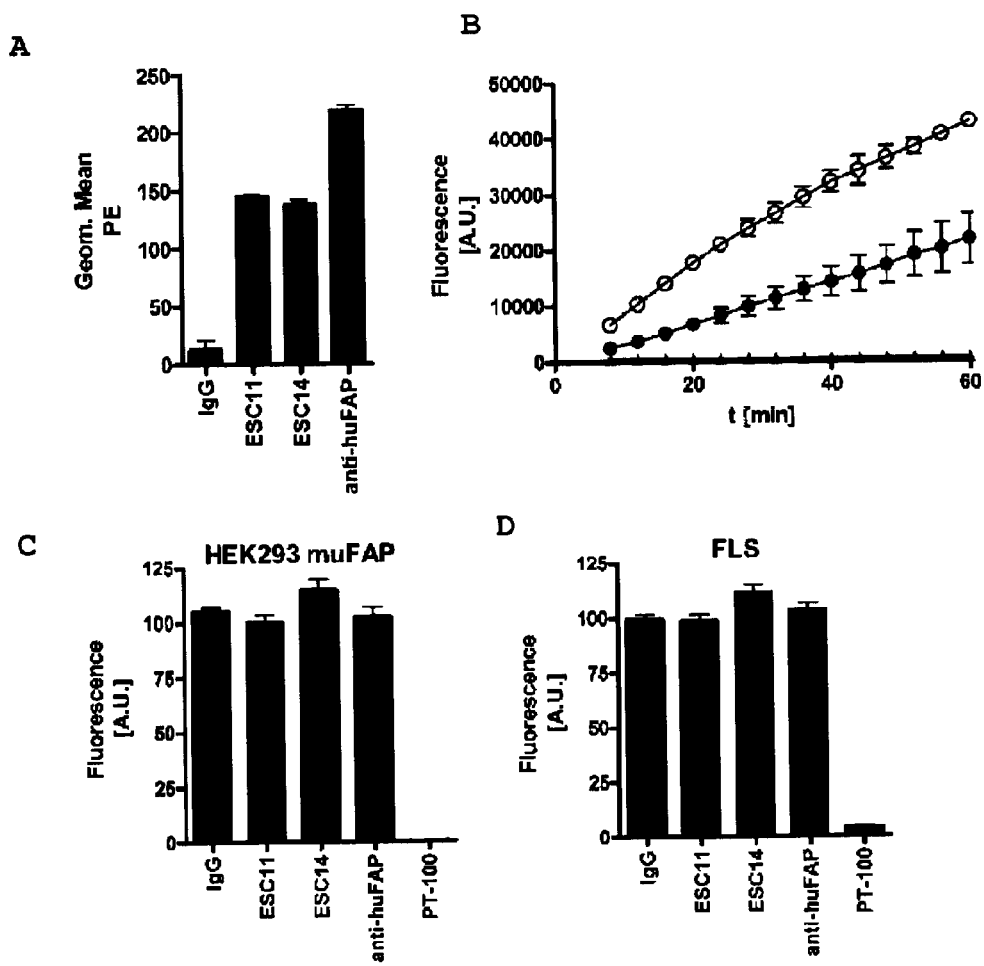
FIGS. 7A, B, C and D: A. Detection of FAP expressed on AF by flow cytometry with 10 μg/ml anti-FAP antibodies. B. Time course of DPP activity in membrane extracts of HEK293 muFAP+ (open circles), HEK293 (closed triangles), and AF (closed circles) as detected by incubation with Ala-Pro-AFC as substrate. C. Effects of antibodies and the synthetic DPP-inhibitor PT-100 on DPP activity in Hek 293 muFAP+ extracts and D. in extracts prepared from AF.

We analysed the effect of both antibodies on dipeptidylpeptidase activity of FAP using cultured human activated fibroblasts (AF) expressing FAP at high levels (12). First, binding of the novel anti-FAP antibodies to native FAP expressed on human AF was assessed by flow cytometry (FIG. 7A). In accordance to competitive binding of ESC11 and ESC 14 on FAP-transfected cells, both antibodies stained AF at slightly lower levels when compared to anti-huFAP antibody, suggesting again a different epitope for ESC11/ESC 14 and anti-huFAP, respectively. Extracts of AF exhibited pronounced DPP activity as detected in an in-vitro assay using Ala-Pro-AFC as substrate (FIG. 7B). The addition of 30 µg/ml IgGs to the extracts of human AF did not affect protease activity (FIG. 7C). In contrast, enzymatic activity was completely blocked by the addition of 100 µM PT-100, a boronic acid inhibitor of DPP activity. Thus, neither antibody is capable to directly impact on DPP enzymatic activity (FIG. 7D). However, there is an indirect impact on DDP activity since our antibodies reduce in a dose-dependent manner the expression level of FAP on target cells (s. below).

Figure 8:
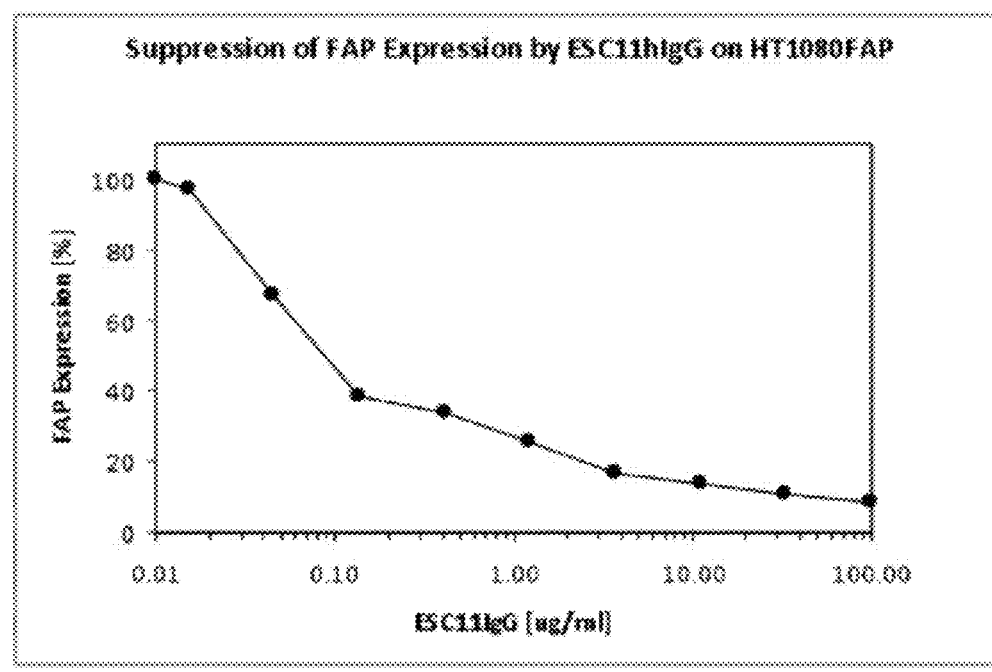
FIG. 8: Downregulation of FAP after cross-linking by bivalent ESC11 IgG. ESC11 IgG and ESC14 IgG (data not shown) mediated a dose-dependent reduction of FAP. The effect could not been observed for monovalent ESC11/ESC14 Fab fragments or the bivalent anti-huFAP antibody.
Figure 9:
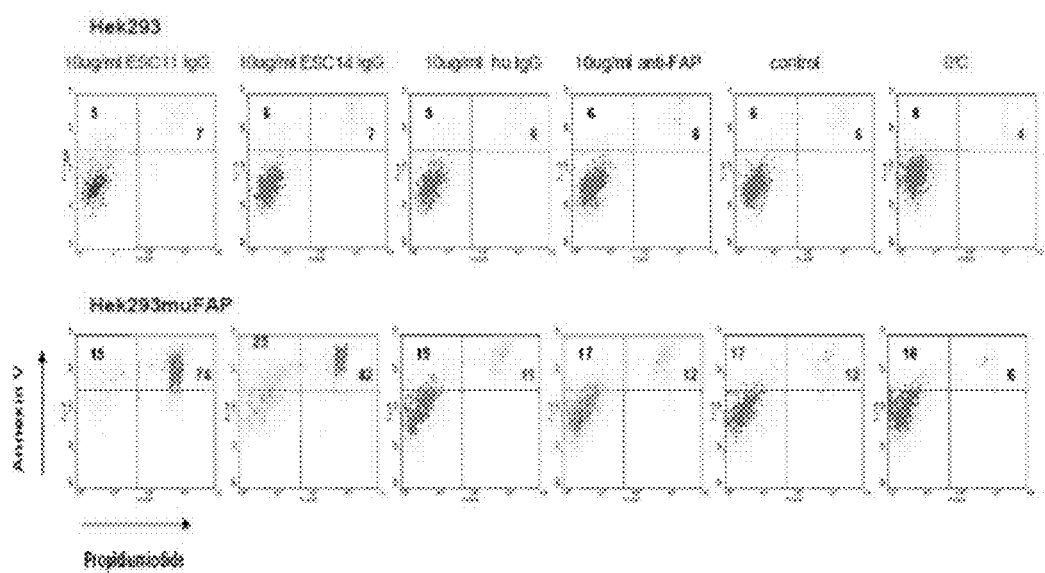
FIG. 9: Induction of apoptosis in HEK293 cells stably transfected with mouse FAP upon incubation with ESC11 and ESC14. Death signalling only occurred in FAP-expressing cells. Survival signalling was neither interrupted following incubation with both antibodies at 4° C., nor after addition of the F19 anti-FAP antibody.

ESC11 and ESC14 IgG Down-Regulate FAP Expression, Disrupt Attachment of Targeted Cells to ECM Proteins and Induce Apoptosis Apart from its enzymatic activity, FAP has the ability to associate with CD26 and form heteromeric complexes that contribute to the invasive phenotype. FAP expression on transfected tumor cell lines could be abolished by ESC11 and ESC14 antibody since both, after bivalent binding to the FAP antigen, induced rapid FAP down-regulation (FIG. 8). To test the impact of ESC11 and ESC14 on the attachment of targeted cells to ECM-proteins, a competition assay was performed. Both mAbs significantly inhibited the binding of FAP-expressing cells to matrigel and to type I collagen (data not shown). The F19 anti-FAP antibody did not interfere with the attachment to ECM proteins. As expected, binding of FAP-negative cells was not altered at all. Induction of apoptosis pathways was studied in a second step [29]. HEK293 cells stably transfected with mouse FAP were incubated with ESC11 and ESC14 and underwent apoptosis, while mock-transfected cells were not altered at all (FIG. 9). The extent of apoptosis induction was superior after the addition of ESC11 when compared to ESC14. Apoptosis could not be induced at 0° C. even in the presence of both antibodies, ESC11 and ESC14. In addition, neither the mF19 nor a control antibody induced any significant level of apoptosis.

Discussion

This is the first report of fully human, mouse/human cross-reactive, high affinity anti-FAP antibodies that induce relevant regulatory activities on target cells pointing out to their therapeutic impact. Since FAP has attracted increased interest as a target for antibody based immunotherapy, data of therapeutically active native FAP-specific antibodies are missing to date. The monoclonal antibody F19 was the first antibody investigated in a phase I clinical trial targeting metastatic colorectal cancer [30]. This trial served as a proof of principle for anti-FAP based tumor stroma targeting [1]. Although patients included in the trial had extensive scarring due to surgery, no specific enrichment of [131]I-F19 could be detected at these sites. There were no toxic side effects associated with intravenous administration of iodine[131] labelled F19 and carcinoma lesions were specifically detected by imaging down to a size of 1 cm in diameter. With regard to the immunogenicity of murine antibodies in humans, recent phase I and phase II clinical trials were conducted using the humanized version of F19, called Sibrotuzumab [31, 32]. Results from these trials demonstrated the safe and well tolerated administration of Sibrotuzumab. Similar to the results obtained in the pivotal phase I trial [30], trace-labelling with $^{131}$I and imaging analysis revealed the specific accumulation of Sibrotuzumab at the tumor area. Unfortunately, unconjugated Sibrotuzumab demonstrated no anti-tumor or any therapeutic activity, respectively [32]. Albeit the biologic function of FAP is still not known in detail, its dipeptidyl peptidase activity was postulated to be involved in tumor progression and metastasis [15, 33]. The lack of Sibrotuzumab to affect FAP enzymatic function was suggested to be the reason for the lack of therapeutic efficacy [34]. In consequence, anti-FAP directed polyclonal antibodies have been raised in order to inhibit the catalytic activity in-vitro. Indeed, treatment of FAP-positive xenografts with anti-FAP anti-sera attenuated tumor growth [13]. However, since polyclonal sera were raised by immunization of rabbits with murine FAP, it is most likely that additional epitopes, different from the catalytic domain, have also been targeted. Therefore, it is difficult to conclude from this study that anti-tumor effects seen really depended on dipeptidyl-peptidase inhibition. These concerns are supported by work with catalytic mutants, reporting a functional impairment of FAP-related bioactivities independent from catalytic function that could also influence tumor growth and invasive cell behaviour [35, 36]. In addition, recent results demonstrated that FAP's proteolytic activity was not necessary for increased adhesion, migration and invasion of FAP over-expressing human hepatic stellate cells [22]. Focal cell adhesion to ECM proteins is mediated by the integrin family of transmembrane adhesion proteins and FAP is known to associate with β1 integrin [19]. This complex is thought to participate in the formation of functional invadopodia [21]. In addition, FAP and DPPIV also form complexes that are localised at invadopodia of fibroblasts on collagenous fibres, thereby facilitating cell migration [37, 38]. As cellular adhesion to ECM proteins is the first step in the progression of invasive and metastatic diseases [39], its significant inhibition resulting from FAP-targeting by novel ESC11 and ESC14 antibodies provides therapeutic impact by disturbing the network architecture of the connective tissue. The observation that the antibody mediated interruption of the cell movement process does not depend on FAP's proteolytic activity is in accordance to above-mentioned data. Since we recently demonstrated that inhibition of dipeptidyl peptidase activity in vivo even significantly promoted the invasion of FAP-expressing fibroblasts (Ospelt et al., submitted), the proteolytically neutral activity of both antibodies should even be advantageous in view of the aimed therapeutic impact. The functional activity of both novel antibodies together with the fact that they do not compete with F19 for FAP binding, suggest targeting of epitopes involved in the formation of supra-molecular complexes.

FAP targeting with ESC11/ESC14 IgG resulted in down-regulation of FAP expression and induced profound behavioural changes in signalling pathways as the disruption of cell adhesion capabilities. This supports a unique mode of action for ESC11 and ESC14 by interfering with complexes consisting of FAP and other components. Involvement of surface serine proteases in apoptosis was demonstrated for CD26, as interruption of survival signalling pathways was mediated through intrinsic and extrinsic apoptotic pathways upon restoration of neuroblastoma cells with DPPIV [29]. Furthermore, induction of late apoptosis in DPPIV-positive mesothelioma cells was reported upon cross-linking of a humanized anti-DPPIV antibody [40]. However, this trial was performed in T-cell deficient SCID-mice and antibody based targeting of DPPIV as an anticancer strategy in humans will be up against the ubiquitous expression of DPPIV that includes T-cells. This major obstacle even built the rationale for the pre-absorption step of selected FAP binders on immunoprecipitated DPPIV to exclude unwanted binding of DPPIV. Association with survival signalling has not yet been identified for FAP and only the novel rational displayed anti-FAP antibodies ESC11 and ESC14 are linked to apoptosis induction upon FAP-targeting. In conclusion, this is the first report of antigen specific and highly effective, multifunctional anti-FAP antibodies with cross-reactivity for human and mouse FAP displaying a therapeutic profile. With regard to the restricted expression of FAP, our data strongly provide evidence for a clinical use of ESC11 and ESC14 in antibody-based therapeutic strategies targeting FAP in invasive diseases.

REFERENCES

1. Rettig, W. J., et al., *Cell-surface glycoproteins of human sarcomas: differential expression in normal and malignant tissues and cultured cells*. Proc Natl Acad Sci USA, 1988. 85(9): p. 3110-4.
2. Rettig, W. J., et al., *Regulation and heteromeric structure of the fibroblast activation protein in normal and transformed cells of mesenchymal and neuroectodermal origin*. Cancer Res, 1993. 53(14): p. 3327-35.
3. Pineiro-Sanchez, M. L., et al., *Identification of the 170-kDa melanoma membrane-bound gelatinase (seprase) as a serine integral membrane protease*. J Biol Chem, 1997. 272(12): p. 7595-601.
4. Scanlan, M. J., et al., *Molecular cloning of fibroblast activation protein alpha, a member of the serine protease family selectively expressed in stromal fibroblasts of epithelial cancers*. Proc Natl Acad Sci USA, 1994. 91(12): p. 5657-61.
5. Goldstein, L. A., et al., *Molecular cloning of seprase: a serine integral membrane protease from human melanoma*. Biochim Biophys Acta, 1997. 1361(1): p. 11-9.
6. Morimoto, C., et al., *Role of CD26/dipeptidyl peptidase IV in human immunodeficiency virus type 1 infection and apoptosis*. Proc Natl Acad Sci USA, 1994. 91(21): p. 9960-4.
7. Garin-Chesa, P., L. J. Old, and W. J. Rettig, *Cell surface glycoprotein of reactive stromal fibroblasts as a potential antibody target in human epithelial cancers*. Proc Natl Acad Sci USA, 1990. 87(18): p. 7235-9.
8. Lee, K. N., et al., *Antiplasmin-cleaving enzyme is a soluble form of fibroblast activation protein*. Blood, 2006. 107(4): p. 1397-404.
9. Bauer, S., et al., *Fibroblast activation protein is expressed by rheumatoid myofibroblast-like synoviocytes*. Arthritis Res Ther, 2006. 8(6): p. R171.
10. Levy, C. E., et al., *Conductive hearing loss in individuals with fibrodysplasia ossificans progressiva*. Am J Audiol, 1999. 8(1): p. 29-33.
11. Acharya, P. S., et al., *Fibroblast activation protein: a serine protease expressed at the remodeling interface in idiopathic pulmonary fibrosis*. Hum Pathol, 2006. 37(3): p. 352-60.
12. Aertgeerts, K., et al., *Structural and kinetic analysis of the substrate specificity of human fibroblast activation protein alpha*. J Biol Chem, 2005. 280(20): p. 19441-4.

13. Cheng, J. D., et al., *Promotion of tumor growth by murine fibroblast activation protein, a serine protease, in an animal model.* Cancer Res, 2002. 62(16): p. 4767-72.
14. Kelly, T., *Evaluation of seprase activity.* Clin Exp Metastasis, 1999. 17(1): p. 57-62.
15. Park, J. E., et al., *Fibroblast activation protein, a dual specificity serine protease expressed in reactive human tumor stromal fibroblasts.* J Biol Chem, 1999. 274(51): p. 36505-12.
16. Edosada, C. Y., et al., *Selective inhibition of fibroblast activation protein protease based on dipeptide substrate specificity.* J Biol Chem, 2006. 281(11): p. 7437-44.
17. Loster, K., et al., *The cysteine-rich region of dipeptidyl peptidase IV (CD 26) is the collagen-binding site.* Biochem Biophys Res Commun, 1995. 217(1): p. 341-8.
18. Artym, V. V., et al., *Molecular proximity of seprase and the urokinase-type plasminogen activator receptor on malignant melanoma cell membranes: dependence on beta1 integrins and the cytoskeleton.* Carcinogenesis, 2002. 23(10): p. 1593-601.
19. Kennedy, A., et al., *Elevation of seprase expression and promotion of an invasive phenotype by collagenous matrices in ovarian tumor cells.* Int J Cancer, 2009. 124(1): p. 27-35.
20. Ghersi, G., et al., *Regulation of fibroblast migration on collagenous matrix by a cell surface peptidase complex.* J Biol Chem, 2002. 277(32): p. 29231-41.
21. Mueller, S. C., et al., *A novel protease-docking function of integrin at invadopodia.* J Biol Chem, 1999. 274(35): p. 24947-52.
22. Wang, X. M., et al., *Fibroblast activation protein increases apoptosis, cell adhesion, and migration by the LX-2 human stellate cell line.* Hepatology, 2005. 42(4): p. 935-45.
23. Monsky, W. L., et al., *A potential marker protease of invasiveness, seprase, is localized on invadopodia of human malignant melanoma cells.* Cancer Res, 1994. 54(21): p. 5702-10.
24. Wolf, B. B., et al., *On the edge of validation—cancer protease fibroblast activation protein.* Mini Rev Med Chem, 2008. 8(7): p. 719-27.
25. Cohen, S. J., et al., *Fibroblast activation protein and its relationship to clinical outcome in pancreatic adenocarcinoma.* Pancreas, 2008. 37(2): p. 154-8.
26. Henry, L. R., et al., *Clinical implications of fibroblast activation protein in patients with colon cancer.* Clin Cancer Res, 2007. 13(6): p. 1736-41.
27. Hoogenboom, H. R., P. Henderikx, and H. de Haard, *Creating and engineering human antibodies for immunotherapy.* Adv Drug Deliv Rev, 1998. 31(1-2): p. 5-31.
28. Cheng, J. D., et al., *Abrogation of fibroblast activation protein enzymatic activity attenuates tumor growth.* Mol Cancer Ther, 2005. 4(3): p. 351-60.
29. Arscott, W. T., et al., *Suppression of neuroblastoma growth by dipeptidyl peptidase IV: relevance of chemokine regulation and caspase activation.* Oncogene, 2009. 28(4): p. 479-91.
30. Welt, S., et al., *Antibody targeting in metastatic colon cancer: a phase I study of monoclonal antibody F19 against a cell-surface protein of reactive tumor stromal fibroblasts.* J Clin Oncol, 1994. 12(6): p. 1193-203.
31. Scott, A. M., et al., *A Phase I dose-escalation study of sibrotuzumab in patients with advanced or metastatic fibroblast activation protein positive cancer.* Clin Cancer Res, 2003. 9(5): p. 1639-47.
32. Hofheinz, R. D., et al., *Stromal antigen targeting by a humanised monoclonal antibody: an early phase II trial of sibrotuzumab in patients with metastatic colorectal cancer.* Onkologie, 2003. 26(1): p. 44-8.
33. Niedermeyer, J., et al., *Mouse fibroblast-activation protein—conserved Fap gene organization and biochemical function as a serine protease.* Eur J Biochem, 1998. 254(3): p. 650-4.
34. Cheng, J. D. and L. M. Weiner, *Tumors and their microenvironments: tilling the soil. Commentary re: A. M Scott et al., A Phase I dose-escalation study of sibrotuzumab in patients with advanced or metastatic fibroblast activation protein-positive cancer. Clin. Cancer Res., 9: 1639-1647, 2003.* Clin Cancer Res, 2003. 9(5): p. 1590-5.
35. Ramirez-Montagut, T., et al., *FAPalpha, a surface peptidase expressed during wound healing, is a tumor suppressor.* Oncogene, 2004. 23(32): p. 5435-46.
36. Wesley, U. V., et al., *A role for dipeptidyl peptidase IV in suppressing the malignant phenotype of melanocytic cells.* J Exp Med, 1999. 190(3): p. 311-22.
37. Chen, W. T., T. Kelly, and G. Ghersi, *DPPIV, seprase, and related serine peptidases in multiple cellular functions.* Curr Top Dev Biol, 2003. 54: p. 207-32.
38. Ghersi, G., et al., *The protease complex consisting of dipeptidyl peptidase IV and seprase plays a role in the migration and invasion of human endothelial cells in collagenous matrices.* Cancer Res, 2006. 66(9): p. 4652-61.
39. Friedl, P. and K. Wolf, *Proteolytic interstitial cell migration: a five-step process.* Cancer Metastasis Rev, 2009. 28(1-2): p. 129-35.
40. Inamoto, T., et al., *Humanized anti-CD26 monoclonal antibody as a treatment for malignant mesothelioma tumors.* Clin Cancer Res, 2007. 13(14): p. 4191-200.

Example 2

The following studies demonstrate rapid internalization of FAP-antibody complexes in FAP expressing cells. HT1080FAP cells were incubated with fluorescence labelled anti-FAP antibody Esc11 DYLIGHT® 4488 (flurorochrome conjugated antibody, ThermoScientific). Incubation of HT1080FAP at 4° C. revealed a specific membrane staining pattern for FAP (FIG. 11A). When cells were warmed up to 37° C., rapid internalisation of FAP-Esc11 complexes could be detected with cytoplasmatic spots and vesicular accumulation (FIG. 11B). An acidic cell wash to strip off any remaining cell surface bound Esc11 two hours after the start of incubation did not change the pattern, indicating that most of the antibody had already internalised after two hours.

Methods: HT1080FAP were grown on fibronectin coated glas slides over night. The cells were then treated with DYLIGHT® (Thermo Scientific) labeled ESC11IgG at either 4° C. or 37° C. for indicated time points. The cover slides were then mounted with flouromount for fluorescence microscopy. ESC11 DYLIGHT® 488 was detected at extention wavelaength of 488 nm and an emission of 518 nm. The results are depicted in FIG. 11.

This invention may be embodied in other forms or carried out in other ways without departing from the spirit or essential characteristics thereof. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. An isolated antibody or fragment thereof which recognizes human and mouse FAP and does not react with CD26 (DPPIV) and comprises the heavy chain variable region CDR domain sequences as set out in SEQ ID NOs: 11, 12 and 13 and the light chain variable region CDR domain sequences set out in SEQ ID NOs: 17, 18 and 19, or highly homologous variants thereof comprising 1 to 3 amino acid substitutions in one or more CDR region, wherein said variants retain human FAP reactivity and lack CD26 reactivity.

2. The isolated antibody or fragment of claim 1 which does not directly affect dipeptidyl peptidase activity of FAP.

3. The isolated antibody or fragment of claim 1 which is an antibody or antibody fragment comprising a heavy chain variable region comprising the amino acid sequence set out in SEQ ID NO: 2 and a light chain variable region comprising the amino acid sequence set out in SEQ ID NO:3.

4. The isolated antibody or fragment of claim 1, wherein said isolated antibody is a diabody, triabody, or tetrabody wherein at least one heavy chain variable region comprises CDR domain sequences as set out in SEQ ID NOs: 11, 12 and 13 and at least one light chain variable region comprises CDR domain sequences set out in SEQ ID NOs: 17, 18 and 19 or the fragment is an antibody F(ab')2 or an scFv fragment.

5. The isolated antibody or fragment of claim 1 further comprising a detectable or functional label.

6. The isolated antibody of claim 5, wherein said detectable or functional label is a covalently attached drug or wherein said label is a radiolabel.

7. A kit for the diagnosis or prognosis of cancer in which FAP antigen is expressed, said kit comprising an antibody or fragment of any one of claim 1 or 3, optionally with reagents and/or instructions for use.

8. A pharmaceutical composition comprising an antibody or fragment as defined in any one of claim 1 or 3 and a pharmaceutically acceptable vehicle, carrier or diluent.

9. A kit for the treatment of a tumor in a human patient, comprising a pharmaceutical dosage form of the pharmaceutical composition of claim 8, and a separate pharmaceutical dosage form comprising an additional anti-cancer agent selected from the group consisting of chemotherapeutic agents, radioimmunotherapeutic agents, and combinations thereof.

* * * * *